(12) United States Patent
Sharma et al.

(10) Patent No.: US 12,408,825 B2
(45) Date of Patent: Sep. 9, 2025

(54) MEDICAL SYSTEMS, DEVICES, AND RELATED METHODS

(71) Applicants: Boston Scientific Scimed, Inc., Maple Grove, MN (US); Boston Scientific Medical Device Limited, Galway (IE)

(72) Inventors: Deepak Kumar Sharma, Uttar Pradesh (IN); Nabarun Bhowmick, West Bengal (IN); Shrikant Vasant Raut, Maharashtra (IN); James J. Scutti, Norwell, MA (US); Sharath Kumar G, Karnataka (IN)

(73) Assignees: Boston Scientific Scimed, Inc., Maple Grove, MN (US); Boston Scientific Medical Device Limited, Galway (IE)

( * ) Notice: Subject to any disclaimer, the term of this patent is extended or adjusted under 35 U.S.C. 154(b) by 500 days.

(21) Appl. No.: 17/849,799

(22) Filed: Jun. 27, 2022

(65) Prior Publication Data

US 2023/0000313 A1 Jan. 5, 2023

Related U.S. Application Data

(60) Provisional application No. 63/216,548, filed on Jun. 30, 2021.

(51) Int. Cl.
*A61B 1/005* (2006.01)
*A61B 17/00* (2006.01)
(Continued)

(52) U.S. Cl.
CPC .......... *A61B 1/0057* (2013.01); *A61B 1/0052* (2013.01); *A61B 1/0055* (2013.01);
(Continued)

(58) Field of Classification Search
CPC ... A61B 1/0057; A61B 1/0052; A61B 1/0055; A61B 18/1492; A61B 2017/003;
(Continued)

(56) References Cited

U.S. PATENT DOCUMENTS 5,397,304 A * 3/1995 Truckai ............ A61M 25/0147
604/528
2007/0250000 A1 10/2007 Magnin et al.
(Continued)

FOREIGN PATENT DOCUMENTS

WO WO-2014077893 A1 * 5/2014 ............ A61F 2/246

OTHER PUBLICATIONS

International Search Report and Written Opinion in International Application No. PCT/US2022/035049, mailed Oct. 17, 2022 (12 pages).

*Primary Examiner* — Linda C Dvorak
*Assistant Examiner* — Abigail Bock
(74) *Attorney, Agent, or Firm* — Bookoff McAndrews PLLC

(57) ABSTRACT

A medical device system includes an insertion device and a medical device. The insertion device includes an insertion device handle, including a port on a handle body. The insertion device also includes an insertion device shaft extending from the insertion device handle. The insertion device shaft includes a working channel connected to the port. The medical device includes a medical device handle, including a movable handle portion and a stationary handle portion. The movable handle portion includes a ball portion movably positioned within a cavity in the stationary handle portion. The medical device also includes a medical device shaft. The medical device shaft is configured to be delivered through the port in the insertion device handle and through the working channel in the insertion device shaft. Movement (Continued)

of the movable handle portion relative to the stationary handle portion controls movement of a distal portion of the medical device shaft.

19 Claims, 17 Drawing Sheets

(51) Int. Cl.
    *A61B 18/00*     (2006.01)
    *A61B 18/14*     (2006.01)

(52) U.S. Cl.
    CPC .... A61B 18/1492 (2013.01); *A61B 2017/003* (2013.01); *A61B 2018/00595* (2013.01); *A61B 2018/0091* (2013.01); *A61B 2018/144* (2013.01); *A61B 2018/1475* (2013.01)

(58) Field of Classification Search
    CPC .. A61B 2018/00595; A61B 2018/0091; A61B 2018/144; A61B 2018/1475
    See application file for complete search history.

(56) References Cited

U.S. PATENT DOCUMENTS

| | | |
|---|---|---|
| 2014/0276808 A1 | 9/2014 | Gittard et al. |
| 2015/0196364 A1 | 7/2015 | Perez, III et al. |
| 2020/0170738 A1 | 6/2020 | Hasegawa |

\* cited by examiner

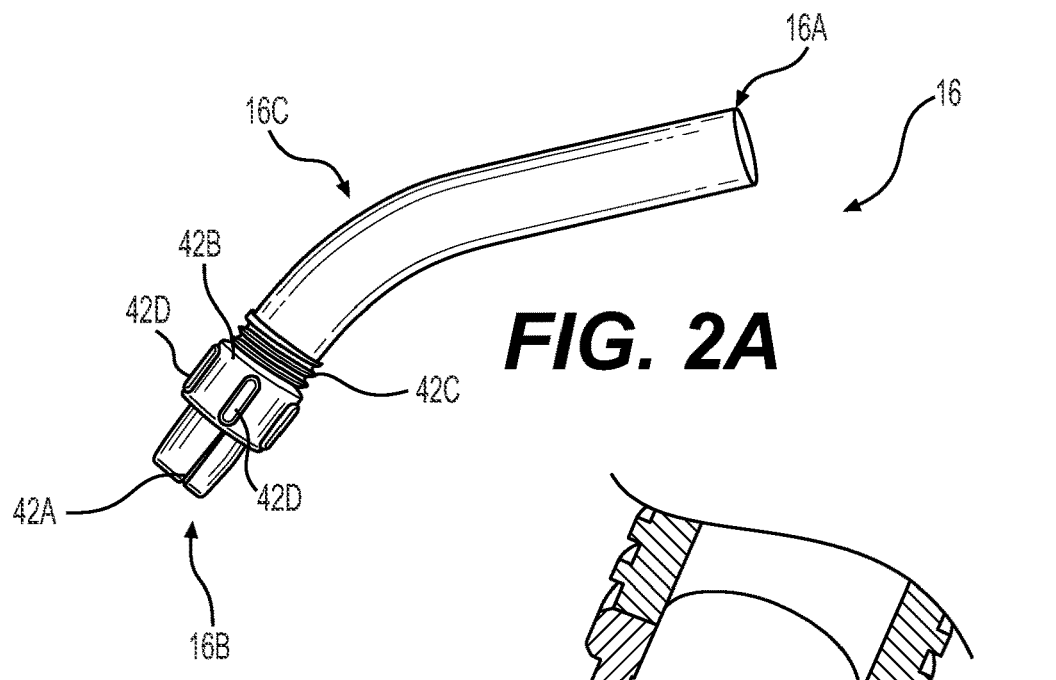
FIG. 2A
FIG. 2B
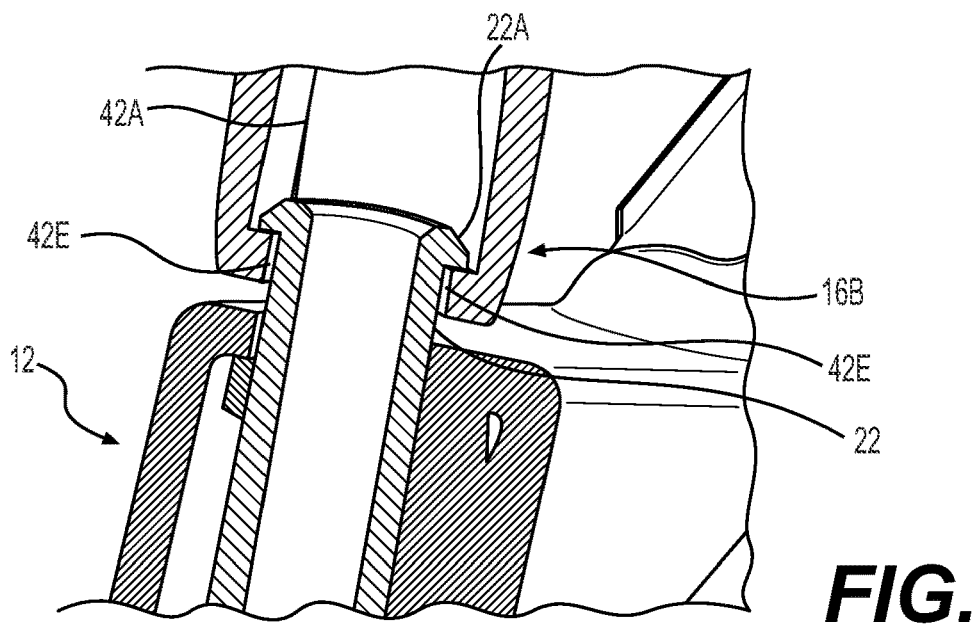
FIG. 2C

MEDICAL SYSTEMS, DEVICES, AND RELATED METHODS

CROSS-REFERENCE TO RELATED APPLICATIONS

This present disclosure claims priority to U.S. Provisional Patent Application No. 63/216,548, filed on Jun. 30, 2021, the disclosure of which is incorporated herewith by reference.

TECHNICAL FIELD

Various aspects of this disclosure generally relate to medical systems, devices, and methods for manipulating or treating tissue or other material within a body. In particular, aspects of the disclosure relate to medical systems, devices, and methods for performing a medical procedure using, in some embodiments, a medical device capable of being inserted through an insertion device and into the body to treat a treatment site and deflecting or otherwise positioning the medical device relative to a distal end of the insertion device.

BACKGROUND

A wide variety of medical techniques and instruments have been developed for diagnosis and/or treatment within a patient's body, such as within a patient's gastrointestinal (GI) tract. Endoscopic sub-mucosal dissection (ESD), endoscopic sub-mucosal resection (ESR), mucosal resection (EMR), polypectomy, mucosectomy, etc., are minimally invasive treatment methods for both malignant and non-malignant lesions. Endoscopic medical procedures, such as, for example, ESR, may be used to excise sessile adenomas or other unwanted tissue (e.g., tumors attached to a bodily surface) from the surface of an anatomical lumen (e.g., stomach, esophagus, colon, etc.). Such procedures often require the resection of one tissue plane while leaving an underlying tissue plane intact, or other precise treatments. Commonly, snares or other medical devices are used during such medical procedures, for resecting tissue from a treatment site. However, many conventional snares or medical devices operate in only one degree of freedom, and deflection of the snare (or another end effector) is often limited and/or dependent on the tip deflection of an endoscope or other device used for insertion into the patient. Furthermore, devices that may allow for separate deflection may require a number of operators, multiple hands, various movements of the hands, wrists, arms, etc. of the operator(s), an increased cognitive load on the operator(s) to obtain the desired movement, and/or other issues These concerns may increase the duration, costs, and risks of the medical procedure. The devices and methods of this disclosure may rectify some of the deficiencies described above or address other aspects of the art.

SUMMARY

Examples of this disclosure relate to, among other things, systems, devices, and methods for performing one or more medical procedures. Each of the examples disclosed herein may include one or more of the features described in connection with any of the other disclosed examples.

In one example, a medical device system may include an insertion device and a medical device. The insertion device may include an insertion device handle, which may include a port on a handle body. The insertion device also may include an insertion device shaft extending from the insertion device handle. The insertion device shaft may include a working channel connected to the port. The medical device may include a medical device handle, which may include a movable handle portion and a stationary handle portion. The movable handle portion may include a ball portion movably positioned within a cavity in the stationary handle portion. The medical device also may include a medical device shaft. The medical device shaft may be configured to be delivered through the port in the insertion device handle and through the working channel in the insertion device shaft. Movement of the movable handle portion relative to the stationary handle portion may control movement of a distal portion of the medical device shaft.

The medical device system may include one or more of the following features. The medical device system may further include a plurality of steering wires. Each of the plurality of steering wires may be coupled to the ball portion at a proximal end and to the distal portion of the medical device shaft at a distal end. The distal ends of the plurality of steering wires may be coupled to a ring at the distal portion of the medical device shaft. The plurality of steering wires may include four steering wires coupled to the ball portion. The ball portion may include four wire mounts at locations 90 degrees apart from each other around a circumference of the ball portion. Each wire mount may include a crimping slot to couple each steering wire to the ball portion. The medical device may include an actuation wire and a movable body coupled to the actuation wire. The actuation wire may be movable relative to the medical device shaft by movement of the movable body relative to the stationary handle portion. The medical device may include a distal electrode, and movement of the movable body may manipulate the actuation wire to extend or retract the distal electrode relative to a distal end of the medical device shaft. The medical device handle may include a fluid port and/or a cautery hub.

The medical device system may further include a cautery hub on the medical device handle and an actuation wire extending through at least a portion of the medical device handle and the medical device shaft. The actuation wire may be electrically connected to the cautery hub. The medical device system may further include an adapter positioned between the port on the handle of the insertion device and the medical device handle. The adapter may include an arced portion and/or may be at least partially flexible. The adapter may be removably coupled to the insertion device and may include one or more slits on a distal portion. The adapter may include a lock nut that is movable along the distal portion to control a width of each of the one or more slits.

The medical device system may further include a guide wire device. The guide wire device may include a guide wire handle and a guide wire. The guide wire may include a main wire portion, a distal wire portion, and a movable pull wire coupled to the distal wire portion. The guide wire handle may include a casing, a roller rotatably coupled to the casing, and a button that is movable within a channel in the roller. The roller may be coupled to the pull wire to control extension and/or rotation of the pull wire. A portion of the pull wire may be coupled to the distal wire portion via a coupling. The coupling may extend over less than an entire outer circumference of the portion of the pull wire. The movable handle portion may be a joystick. The stationary handle body may be a main handle body positioned distal to the joystick.

In another aspect, a medical system may include a medical device and a guide wire device. The medical device may include a medical device handle. The medical device handle may include a movable handle portion and a stationary handle portion. The movable handle portion may include a ball portion movably positioned within a cavity in the stationary handle portion. The medical device may also include a medical device shaft extending from the medical device handle. The medical device may also include a plurality of wires. The plurality of wires may be coupled to the ball portion of the movable handle portion and to a ring at a distal portion of the medical device shaft. Movement of the ball portion of the movable handle portion within the cavity in the stationary handle portion may manipulate a distal portion of the medical device shaft. The guide wire device may include a guide wire handle and a guide wire. The medical device shaft may include one or more openings or tubes along one or more outer portions of the medical device shaft configured to receive a portion of the guide wire.

The medical system may include one or more of the following features. The guide wire device may include a main wire portion, a distal wire portion, and a movable pull wire coupled to the distal wire portion. The guide wire handle may include a casing, a roller rotatably coupled to the casing, and a button that is movable within a channel in the roller. The roller may be coupled to the pull wire to control extension and/or rotation of the pull wire. The medical system may further include an insertion device. The insertion device may include an insertion device handle having a port to receive a portion of the medical device shaft and a portion of the guide wire. The insertion device may also include an insertion device shaft extending from the insertion device handle. The insertion device shaft may include a lumen in communication with the port. The insertion device may also include a control device coupled to a portion of the insertion device handle. The control device may be movable to control a position of a distal end of the insertion device shaft.

In yet another aspect, a medical device may include a medical device handle. The medical device handle may include a joystick portion and a stationary handle portion. The joystick portion may be positioned distal to the stationary handle portion and may include a ball portion movably positioned within a cavity in the stationary handle portion. The medical device may also include a medical device shaft extending from the medical device handle. The medical device may include a plurality of wires. The plurality of wires may be coupled to the ball portion of the joystick portion and to a ring at a distal portion of the medical device shaft. Movement of the ball portion of the movable handle portion within the cavity in the stationary handle portion may manipulate a distal portion of the medical device shaft.

The medical device may include one or more of the following features. The medical device may include a movable body coupled to the stationary handle portion. The medical device may further include an actuation wire extending from the movable body to an end effector at a distal end of the medical device shaft. Movement of the movable body may control an extension or retraction of the end effector.

It may be understood that both the foregoing general description and the following detailed description are exemplary and explanatory only and are not restrictive of the disclosure, as claimed.

BRIEF DESCRIPTION OF THE DRAWINGS

The accompanying drawings, which are incorporated in and constitute a part of this specification, illustrate exemplary aspects of the disclosure and together with the description, serve to explain the principles of the disclosure.

FIGS. 2A-2C illustrate various views of the adapter, according to aspects of this disclosure.

DETAILED DESCRIPTION

The terms "proximal" and "distal" are used herein to refer to the relative positions of the components of an exemplary medical system and exemplary medical devices. When used herein, "proximal" refers to a position relatively closer to the exterior of the body or closer to a medical professional using the medical system or medical device. In contrast, "distal" refers to a position relatively further away from the medical professional using the medical system or medical device, or closer to the interior of the body. As used herein, the terms "comprises," "comprising," "having," "including," or other variations thereof, are intended to cover a non-exclusive inclusion, such that a system, device, or method that comprises a list of elements does not include only those elements, but may include other elements not expressly listed or inherent thereto. Unless stated otherwise, the term "exemplary" is used in the sense of "example" rather than "ideal."

As used herein, the terms "about," "substantially," and "approximately," indicate a range of values within +/−10% of a stated value.

Examples of this disclosure include systems, devices, and methods for facilitating and/or improving the efficacy, efficiency, and/or safety of a medical procedure. Embodiments of the disclosure may relate to systems, devices, and methods for performing various medical procedures and/or treating portions of the large intestine (colon), small intestine, cecum, esophagus, stomach, any other portion of the gastrointestinal tract, lungs, and/or any other suitable patient anatomy. Various embodiments described herein include single-use or disposable medical devices. Some aspects of the disclosure may be used in performing an endoscopic, arthroscopic, bronchoscopic, ureteroscopic, colonoscopic, or other type of procedure. For example, the disclosed aspects may be used with duodenoscopes, bronchoscopes, ureteroscopes, colonoscopes, catheters, diagnostic or therapeutic tools or devices, or other types of medical devices. One or more of the elements discussed herein could be metallic, plastic, or include a shape memory metal (such as nitinol), a shape memory polymer, a polymer, or any combination of biocompatible materials.

Reference will now be made in detail to examples of the disclosure described above and illustrated in the accompanying drawings. Wherever possible, the same reference numbers will be used throughout the drawings to refer to the same or like parts. It is noted that one or more aspects of the medical systems or devices discussed herein may be combined and/or used with one or more aspects of other medical systems or devices discussed herein.

Figure 1:
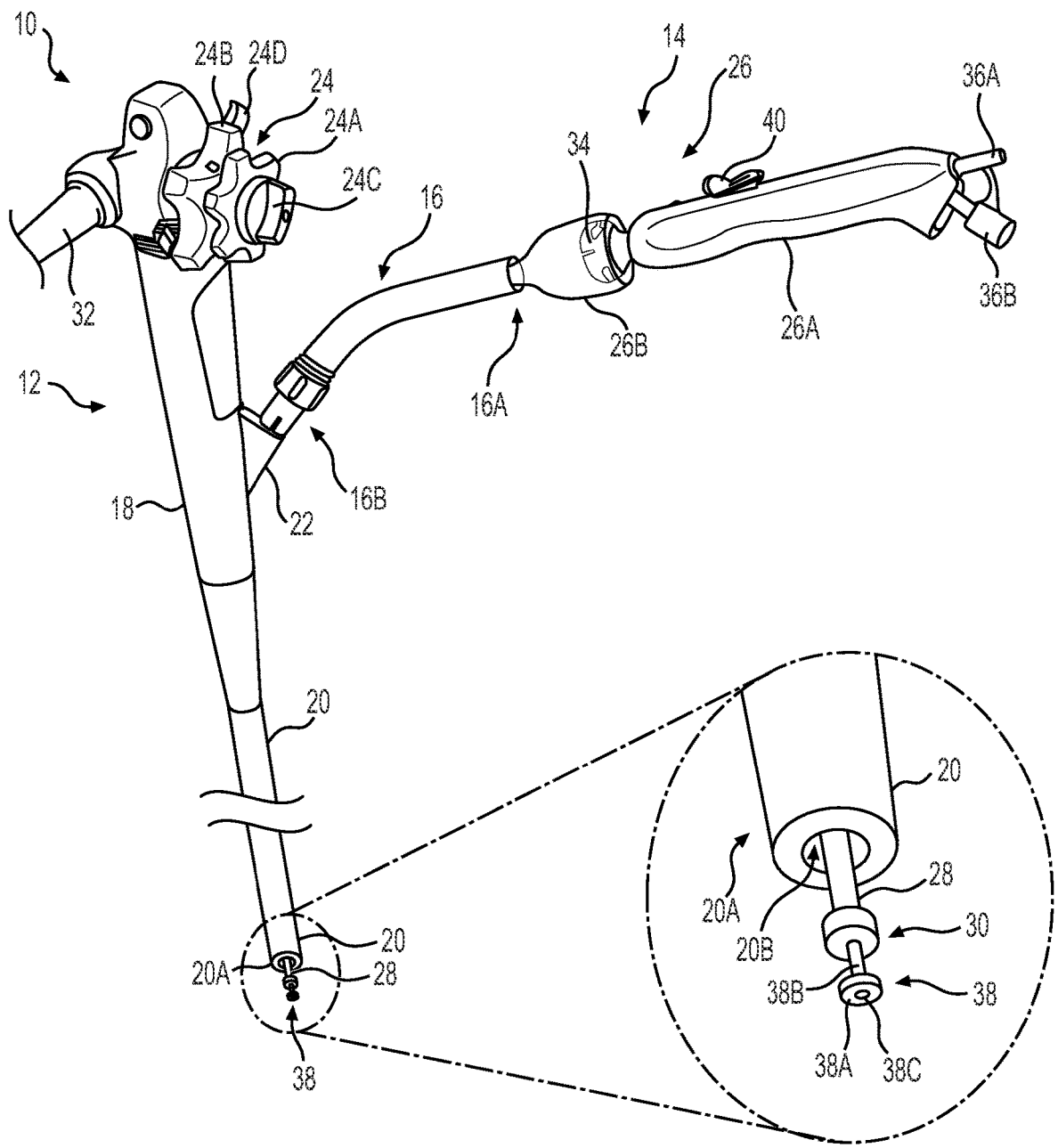
FIG. 1 illustrates a perspective view of an exemplary medical system, including an insertion device, a medical device, and an adapter, according to aspects of this disclosure.

FIG. 1 illustrates a perspective view of an exemplary medical system 10 that includes an insertion device 12, a medical device 14, and an adapter 16. Insertion device 12 includes an insertion device handle 18, including a handle body, and an insertion device shaft 20, for example, extending from a distal end of handle 18 to a distal end 20A. Insertion device 12 also includes at least one working channel (not shown), for example, extending from insertion device handle 18 to a distal opening 20B in distal end 20A. Insertion device 12 also includes a port 22, for example, in handle 18, and port 22 may connect to the working channel. Insertion device 12 may include a control device 24, for example, on a portion of handle 18, and one or more portions of control device 24 may be manipulated (e.g., rotated) to control a deflection of a portion of medical device shaft 20, for example, distal end 20A.

Medical device 14 may include a medical device handle 26 and a medical device shaft 28 extending from medical device handle 26 to a distal end 30. Medical device handle 26 may include a movable handle portion or a main handle body 26A and a stationary handle portion or a joint (e.g., a ball joint), referred to herein as socket body 26B. Main handle body 26A is movable relative to and positioned proximal to socket body 26B. As discussed in detail below, movement of main handle body 26A relative to socket body 26B may control the movement of one or more steering wires (FIGS. 3A, 3D, and 3E) and control a deflection of distal end 30 of medical device shaft 28. Additionally, medical device shaft 28 may be delivered through port 22, for example, via adapter 16, and through the working channel to extend from distal end 20A of shaft 20 of insertion device 12. In these aspects, distal end 30 of medical device shaft 28 may be extended from distal end 20A of insertion device 12, and may be controlled via one or more of control device 24, movement of medical device handle 26 relative to insertion device handle 18, and movement of main handle body 26A relative to socket body 26B.

Insertion device 12 may be a duodenoscope, an endoscope, a colonoscope, an ureteroscope, a bronchoscope, etc., or any other like device having a handle and a shaft. As mentioned, insertion device 12 may include control device 24, for example, on a proximal portion of handle 18. Control device 24 may be movable (e.g., rotatable) relative to handle 12, and may control the movement of a portion (e.g., distal end 20A) of insertion device shaft 20. Control device 24 may include one or more dials or knobs. As shown in FIG. 1, control device 24 may include first and second knobs 24A and 24B, for example, each rotatable to deflect distal end 20A along two different planes. Control device 24 may include one or more locking mechanisms. As shown in FIG. 1, control device 24 may include two locking mechanisms 24C and 24D, for example, each engageable with one of knobs 24A and 24B to lock and/or unlock the position of the knob, and thus lock and/or unlock the position of distal end 20A of insertion device shaft 20. Alternatively, control device 24 may actuate or move one or more elevators in insertion device shaft 20, or otherwise actuate a cable driven function of insertion device 12.

Insertion device 12 may include a conduit 32. For example, insertion device handle 18 may be coupled to conduit 32. Conduit 32 may connect insertion device handle 18 to an external power source, processing software, one or more displays, one or more memory or storage devices, etc., for example, via an umbilicus (not shown). In this aspect, insertion device 12 may include one or more illumination devices and/or cameras at distal end 20A, which may be powered and/or connected to processing software, one or more displays, a memory, etc. via one or more communication wires (not shown) within insertion device 12 and via conduit 32. Additionally, conduit 32 may connect insertion device handle 18 to one or more fluid sources, for example, an air source, a water source, etc. Conduit 32 may also connect insertion device handle 18 to a suction source. In these aspects, one or more valves coupled to or received within one or more apertures (not shown) in insertion device handle 18 may control the delivery of air or water and/or the application of suction through insertion device 12 to the area distal to distal end 20A of insertion device shaft 20.

As mentioned, medical device 14 includes medical device handle 26 and medical device shaft 28 extending from medical device handle 26 to distal end 30. Medical device handle 26 includes main handle body 26A and joint (e.g., a ball joint), referred to herein as socket body 26B, with main handle body 26A being movable relative to socket body 26B. For example, socket body 26B is shown as being partially transparent in FIG. 1. As shown, a distal portion or a ball portion 34 of main handle body 26A may be positioned within socket body 26B. As discussed below, one or more control elements (e.g., steering wires) may be connected to ball portion 34, and the one or more control elements may be coupled to a distal portion of medical device shaft 28. Movement of main handle body 26A relative to socket body 26B may control the movement of the one or more control elements, and also control the deflection of the distal portion (i.e., distal end 30) of medical device shaft 28. Additionally, although not shown, medical device handle 26 may include one or more frictional and/or locking elements to help control and/or lock the relative movement of main handle body 26A relative to socket body 26B.

Medical device handle 26 also may include a port 36A configured to receive fluid, and a hub 36B configured to receive electrical energy similar to an electrical plug or socket. Port 36A and hub 36B may be positioned on proximal portions of medical device handle 26. Distal end 30 of medical device shaft 28 may include an end effector, for example, an energy delivery portion or an electrode portion 38 (hereinafter "electrode 38"). Electrode 38 is electrically connected to hub 36B, and may include a channel fluidly connected to, or otherwise in fluid communication with, port 36A. Additionally, as shown in FIG. 1, electrode 38 may include a distal tip 38A and an electrode shaft 38B. In some aspects, distal tip 38A may be wider (e.g., in a lateral direction away from a longitudinal direction of electrode shaft 38B) than electrode shaft 38B. For example, distal tip 38A may include a mushroom-like or semi-spherical tip. In some aspects, the size and/or shape of distal tip 38A may help the user to deliver energy and/or treat tissue. Furthermore, although not shown, distal end 30 of medical device shaft 28 may include an end cap surrounding a portion of electrode 38, for example, to help insulate medical device shaft 28 from electrode 38.

Medical device handle 26 may include a movable body 40, for example, on a portion of main handle body 26A. Movable body 40 may be a knob or other mechanism movable (e.g., slideable) within a track formed in main handle body 26A, and movable body 40 may control the position of electrode 38, for example, relative to distal end 30 of medical device shaft 28. In this aspect, and as discussed below, medical device 14 may include a pull wire, actuation wire, a drive wire, or other connection(s) between movable body 40 and electrode 38, for example, coupled to electrode shaft 38B. In this example, movement of movable body 40 relative to main handle body 26A in a first direction (e.g., the distal direction) may extend electrode 38 relative to medical device shaft 28 (e.g., move electrode 38 distally relative to a distal end 30 of medical device shaft 28). Similarly, movement of movable body 40 relative to main handle body 26A in a second direction (e.g., the proximal direction) may retract electrode 38 relative to medical device shaft 28 (e.g., move electrode 38 proximally relative to a distal end 30 of medical device shaft 28).

In some aspects, main handle body 26A may be formed of two halves, for example, that form the track in which movable body 40 is movable. For example, although not shown, one half of main handle body 26A may include unthreaded holes, and another half of main handle body 26A may include threaded holes. In this aspect, the halves of main handle body 26A may be coupled via one or more screws. Alternatively, the halves of main handle body 26A may be coupled via an adhesive, a snap-fit, or other appropriate coupling mechanism.

In some aspects, medical device handle 26 may be coupled to a fluid source via port 36A. Port 36A may be in fluid communication with electrode 38 via an internal lumen (not shown), which may extend through medical device handle 26 and medical device shaft 28. In these aspects, electrode 38 may include an internal lumen with one or more outlets 38C, for example, in a distal portion of electrode 38, to deliver fluid to a treatment site, for example, to inject fluid below a layer of tissue (e.g., the mucosal layer) and help lift the layer of tissue. Port 36A may include a one-way valve, a luer, a seal, threading, and/or any appropriate connection or mating element to help maintain a secure connection between medical device handle 26 and the fluid source, minimize or prevent back-flow (e.g., fluid flowing proximally out of port 36A), and/or inhibit, minimize, or prevent leakage. In at least one example, port 36A may include a one-way valve having an outer housing containing an inner elastomeric and/or gelatinous sealing member. Although not shown, one or more lumens, tubes, conduits, channels, etc. may be positioned within insertion device 12 and/or medical device 14 and may fluidly connect port 36A to electrode 38, for example, to deliver fluid out of electrode outlet 38C. In some examples, medical device handle 26 does not include a port 36A, for example, when medical device 14 is not used for fluid delivery.

In some aspects, medical device handle 26 may be coupled to an energy source via hub 36B. Hub 36B may include one or more prongs or pins to couple to the energy source. Hub 36B may be electrically coupled to electrode 38 via one or more conductive elements, which may be electrically coupled to the one or more prongs or pins of hub 36B and extend through medical device handle 26 and through at least a portion of medical device shaft 28. The energy source may be, for example, an electrocautery source, a radio frequency generator, a heating source, a current generator, etc. In other aspects, the energy source may be a part of medical device handle 26 (e.g., an internal battery in medical device handle 26). Although not shown, one or more actuators (e.g., foot pedals, buttons, switches, etc.) may control the delivery of energy from the energy source, and thus control the delivery of energy from electrode 38. Alternatively, medical device 14 may be used to apply suction. In this example, medical device handle 26 may include a suction port, for example, to couple medical device handle 26 and medical device shaft 28 to a suction source.

In at least one aspect, medical device 14 may be used for monopolar electrosurgery, and may include a return electrode positioned remotely from electrode 38 on or otherwise adjacent to the subject. In other aspects, medical device 14 may be used for bipolar electrosurgery. In such instances, electrode 38 may include an active electrode portion, and a return electrode may be provided at or near another portion of electrode 38, medical device shaft 28, and/or insertion device shaft 20. In at least one example, two conductive elements may run through medical device shaft 28, where the conductive elements may be electrically isolated from each other, allowing one conductive element to conduct energy to the active electrode and the other conductive element to conduct energy from a return electrode.

Referring to FIGS. 1 and 2A-2C, adapter 16 may be a substantially tubular element, and may help couple medical device 14 to insertion device 12. Adapter 16 includes a proximal portion 16A, for example, configured to receive a portion of medical device shaft 28, and abut a distal portion of medical device handle 26, for example, a distal portion of socket body 26B. Adapter 16 also includes a distal portion 16B, for example, configured to be coupled to a portion of port 22. As mentioned, adapter 16 may be positioned on or over or otherwise coupled to port 22 of insertion device handle 18, and medical device shaft 28 may be inserted through adapter 16, into port 22, and through the working channel of insertion device 12 to distal end 20A of insertion device shaft 20. Port 22 may include a one-way valve, a luer, a seal, threading, and/or any appropriate connection or mating element to help maintain a secure connection between insertion device handle 18 and adapter 16, inhibit, minimize, or prevent back-flow (e.g., fluid flowing proximally out of port 22), and/or inhibit, minimize, or prevent leakage.

Additionally, adapter 16 may help to form a fulcrum or pivot point for medical device handle 26, for example, such that main handle body 26A may move relative to socket body 26B. Adapter 16 may also help to allow for medical device 14, and thus medical device shaft 28 to move proximally or distally relative to insertion device 12, allowing for distal end 30 of medical device shaft 28 to move relative to insertion device distal end 20A.

Furthermore, distal portion 16B of adapter 16 may include one or more slits 42A, for example, extending longitudinally in a portion of distal portion 16B. In some configurations, a distal portion of the one or more slits 42A may be wider than a proximal portion of the one or more slits 42A. Adapter 16 may also include a lock nut 42B and threading 42C, for example, on distal portion 16B. As shown in FIG. 2A, lock nut 42B may be movable (e.g., rotatable) on threading 42C. Although not shown, lock nut 42B may include an internal threading that is configured to interact with threading 42C. Lock nut 42B may include one or more protrusions or grip features 42D, for example, to help the user manipulate lock nut 42B.

Rotation of lock nut 42B on threading 42C in a first direction (e.g., clockwise) may translate lock nut 42B along adapter 16 in a first direction (e.g., distally), and rotation of lock nut 42B on threading 42C in a second direction (e.g., counterclockwise) may translate lock nut 42B along adapter 16 in a second direction (e.g., proximally). In a distalmost position, lock nut 42B may at least partially overlap with one or more slits 42A. For example, threading 42C may be adjacent to or partially overlap with one or more slits 42A.

Additionally, as shown in FIGS. 2B and 2C, distal portion 16B may also include one or more projections 42E, for example, extending radially inward. As shown in FIG. 2C, port 22 may include one or more extensions 22A, for example, extending radially outward. In this aspect, when adapter 16 is coupled to port 22, projections 42E and extensions 22A may interact to help secure adapter 16 to port 22. For example, with lock nut 42B proximally retracted, distal portion 16B may be in a first configuration, for example, with one or more slits 42A in open configuration(s). Adapter 16 may be positioned over a portion of port 22 of insertion device 12 with distal portion 16B in the first configuration. Then, lock nut 42B may be distally translated, for example, via rotation and interaction with threading 42C. The movement of lock nut 42B may tighten distal portion 16B, for example, by reducing the size or width of slits 42A, and transitioning distal portion 16B into a second configuration, for example, with one or more slits 42A in closed configuration(s). As shown in FIG. 2C, with slits 42A in closed configurations, portions of projection(s) 42E may at least partially abut portions of extension(s) 22A. In the closed configurations, the interaction of projection(s) 42E and extension(s) 22A may, help maintain a secure connection between port 22 and adapter 16, inhibit, minimize, or prevent back-flow (e.g., fluid flowing proximally out of port 22 and/or adapter 16), and/or inhibit, minimize, or prevent leakage.

Adapter 16 may include a bent or arced portion 16C, for example, in a middle portion of adapter 16 between proximal portion 16A and distal portion 16B. Arced portion 16C may help the user to maintain a comfortable, or otherwise suitable, position while handling various components of medical system 10 (e.g., insertion device 12 and medical device 14). In some aspects, adapter 16 may be at least partially flexible, for example, allowing a user to manipulate (e.g., bend) adapter 16 and thus position medical device 14 in a position that is comfortable or otherwise suitable for the user and the medical procedure. Furthermore, although not shown, adapter 16 may include a one-way valve, a luer, a seal, and/or any appropriate connection or mating element to help maintain a secure connection between port 22 and adapter 16 and/or around medical device shaft 28, inhibit, minimize, or prevent back-flow (e.g., fluid flowing proximally out of adapter 16), and/or inhibit, minimize, or prevent leakage.

Figure 3A:
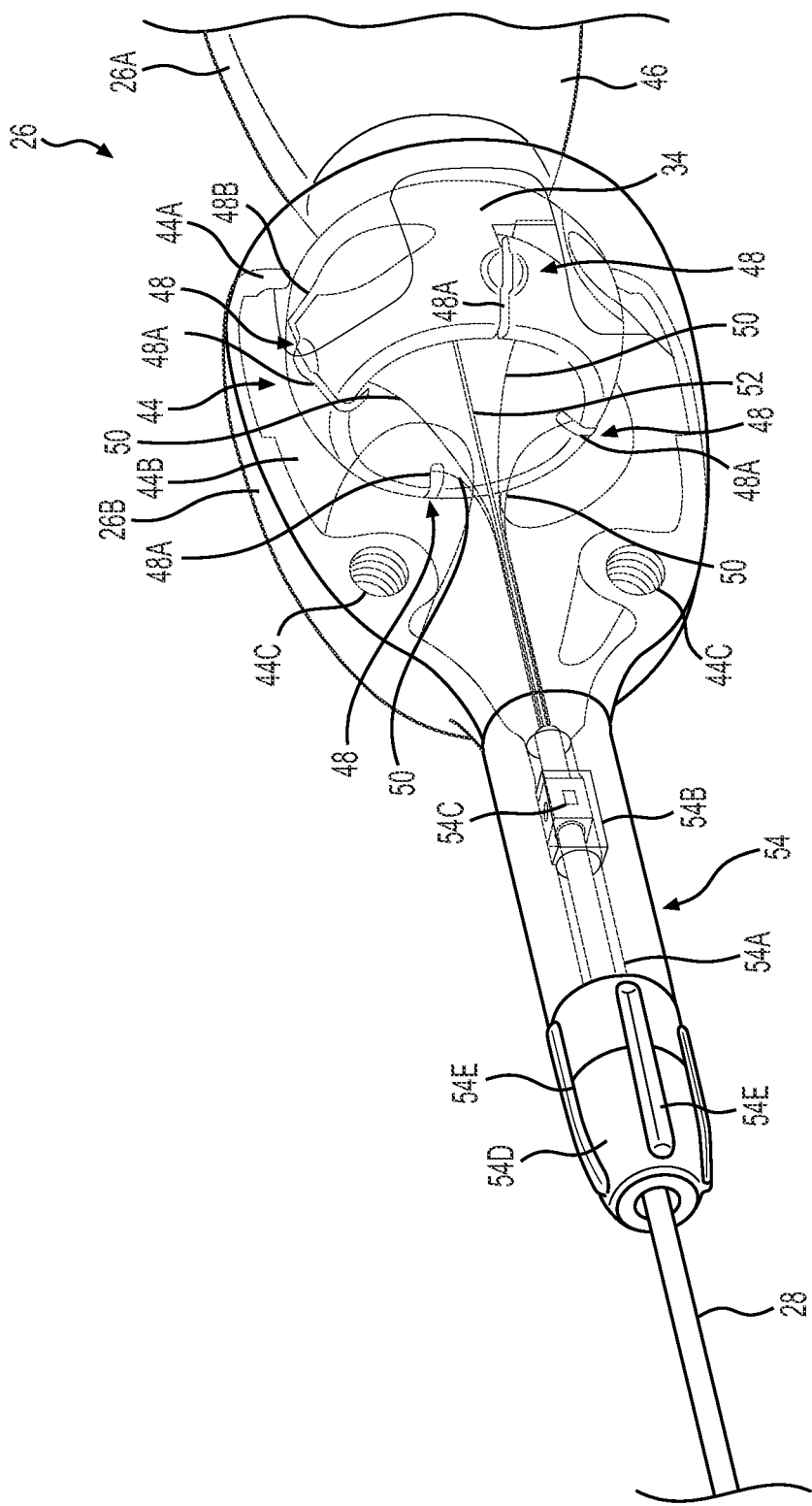
FIGS. 3A-3D illustrate various views of various portions of the medical device, including a medical device handle and a medical device shaft, according to aspects of this disclosure.
Figure 3B:
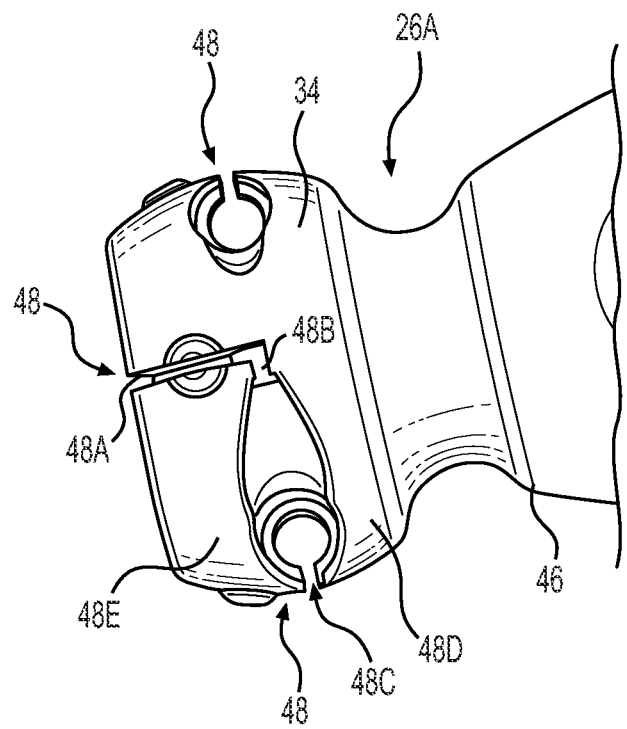
Figure 3C:
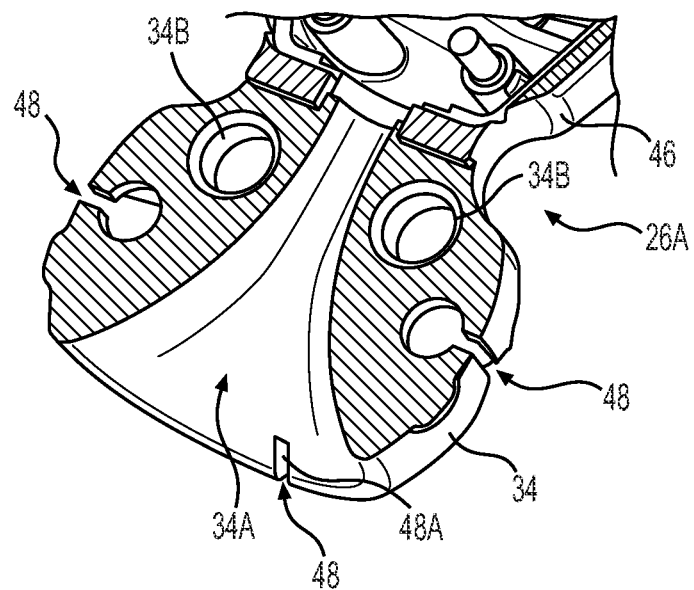
Figure 3D:
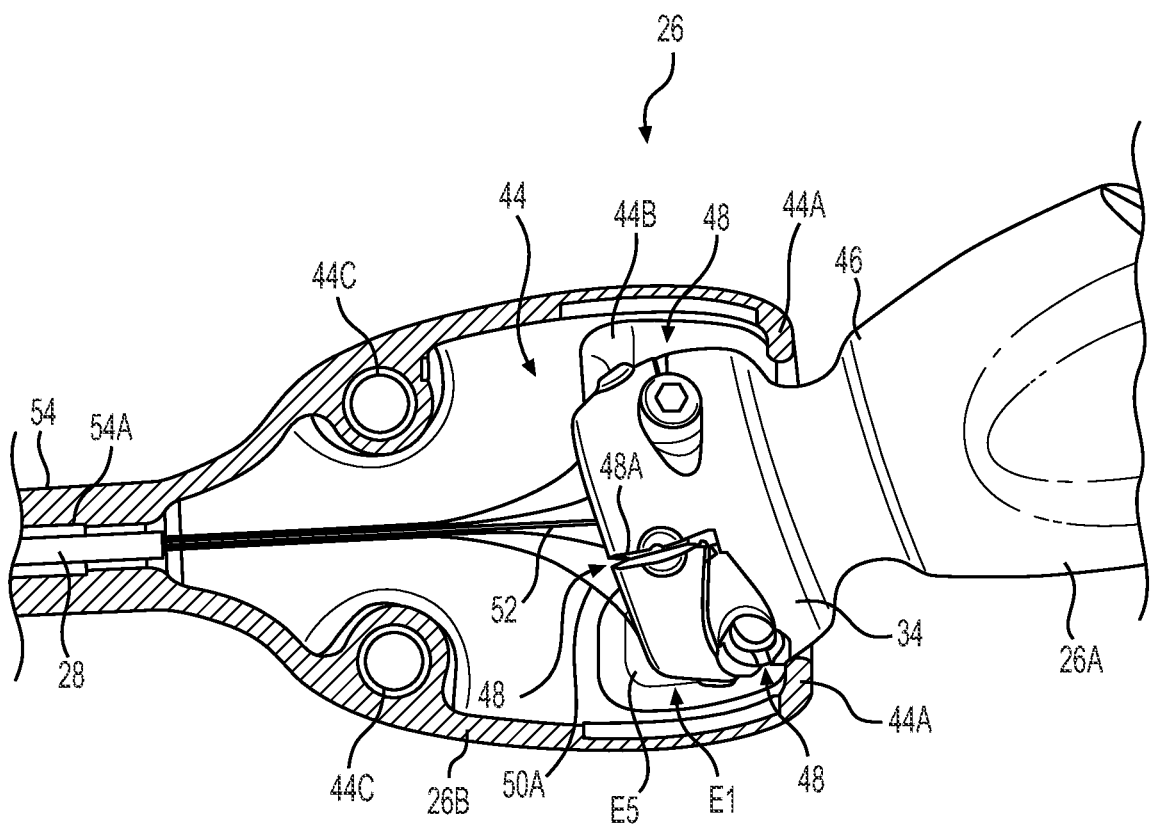

FIGS. 3A-3D illustrate various features of the medical device 14, including main handle body 26A and socket body 26B of medical device handle 26. FIG. 3A illustrates socket body 26B as transparent, allowing internal features of medical device handle 26 to be visible. As shown, ball portion 34 of main handle body 26A may be positioned within a cavity 44 within socket body 26B. As shown in FIGS. 3A and 3D, a proximal portion of cavity 44 may include one or more bulges or ledges 44A, for example, to help retain ball portion 34 within cavity 44. Furthermore, as shown in FIGS. 3A and 3D, socket body 26B may include one or more protrusions 44B, for example, on an inward face of socket body 26B to help form cavity 44. Although not shown, a proximal end of cavity 44 may include one or more gaskets or other sealing elements to help retain ball portion 34 within socket body 26B. Moreover, a portion of main handle body 26A proximal to ball portion 34 may include a widened portion 46, which may help to limit the relative movement of main handle body 26A relative to socket body 26B. As discussed below, ball portion 34 may include one or more wire mounts 48. For example, ball portion 34 may include four wire mounts 48 positioned approximately 90 degrees from each other around a circumference of ball portion 34.

In these aspects, a plurality of steering wires 50 may be coupled to ball portion 34 via wire mounts 48. Movement of ball portion 34, for example, via movement of main handle body 26A relative to socket body 26B, may retract one or more of steering wires 50, for example, to deflect a portion of medical device shaft 28. Additionally, an actuation wire 52 may extend through ball portion 34, socket body 26B, and medical device shaft 28 and to electrode 38, for example, to control the extension or retraction of electrode 38.

Socket body 26B includes cavity 44 to receive a portion of ball portion 34. Socket body 26B may be formed of two halves that are coupled around ball portion 34, for example, via one or more screws, bolts, etc. positioned within coupling holes 44C. In one aspect, coupling holes 44C in one half of socket body 26B may include unthreaded holes, and one half of socket body 26B may include threaded holes. Additionally, socket body 26B includes a cylindrical portion 54. For example, each half of socket body 26B may include a cylindrical portion 54 (i.e., a semi-cylindrical portion), and when the halves of socket body 26B are coupled together, the halves form cylindrical portion 54. Although referred to as a cylindrical portion herein, it is contemplated that portion 54 may have any suitable cross-sectional shape and may be, for example, tapered.

Although not shown, in one or more aspects, main handle body 26A may include a cavity, and socket body 26B may include a ball portion. In this aspect, the ball portion of socket body 26B may be positioned within the cavity of main handle body 26A. In this aspect, main handle body 26A may include one or more wire mounts to couple one or more steering wires to main handle body 26A. Accordingly, movement of main handle body 26A relative to socket body 26B moves (e.g., retracts) the one or more steering wires relative to socket body 26B to deflect a portion of medical device shaft 28.

Cylindrical portion 54 also includes a channel 54A to receive a portion of medical device shaft 28. Additionally, channel 54A may include a widened channel portion or slot 54B. In some aspects, channel 54A may be generally cylindrical, and slot 54B may be generally rectangular. A crimp 54C may be positioned around a portion of medical device shaft 28 within slot 54B, for example, to help couple medical device shaft 28 to medical device handle 26. In this aspect, a portion of medical device shaft 28 and crimp 54C may be positioned within channel 54A and slot 54B of one half of socket body 26B, and then the other half of socket body 26B may be coupled to the first half of socket body 26B to enclose the portion of medical device shaft 28 and crimp 54C. Crimp 54C may move (i.e., proximally and/or distally) within slot 54B as insertion device shaft 20, and thus medical device shaft 28, moves (e.g., bends) within the patient, for example, as insertion device shaft 20 and medical device shaft 28 traverse a tortuous path within the patient. Alternatively, a portion of medical device shaft 28 may be coupled to a portion of medical device handle 26 via heat shrinking or other coupling mechanism.

Medical device handle 18 may also include a handle cap 54D. Handle cap 54D may be coupled to a distal portion of cylindrical portion 54. In some aspects, the distal portion of cylindrical portion 54 may include a threading, and handle cap 54D may include an internal threading, such that handle cap 54D may be screwed onto the distal portion of cylindrical portion 54. Handle cap 54D may also include an internal lumen, which allows medical device shaft 28 to extend from socket body 26B of medical device handle 26. Handle cap 54D may help to couple portions of socket body 26B (e.g., cylindrical portions of two halves). Handle cap 54D may also help to couple medical device shaft 28 to medical device handle 26. In one or more aspects, handle cap 54D may include one or more protrusions or grip features 54E, for example, to help the user manipulate handle cap 54D.

FIG. 3B illustrates a perspective view of ball portion 34 of main handle body 26A, including wire mounts 48. Each wire mount 48 may include a wire slot 48A, for example, extending in a longitudinal direction of main handle body 26A. Wire slots 48A may help align each steering wire 50 with each wire mount 48, which may help prevent steering wire 50 from crimpling, etc. Each wire slot 48A may be connected to or otherwise adjacent to a wire opening 48B, for example, extending approximately perpendicular to wire slot 48A along an outer circumference of ball portion 22. For example, wire openings 48B may be radially inward extending indentations in the outer circumference of ball portion 22. Additionally, wire openings 48B may include crimping slots 48C. Crimping slots 48C may be formed by ball portion 34, for example, by a base portion 48D and an extended portion 48E. In these aspects, one steering wire 50 may be positioned within wire slot 48A, wire opening 48B, and crimping slot 48C. Extended portion 48E may be brought toward (e.g., compressed toward) base portion 48D, for example, with pliers, a vice, or other force applying mechanism, in order to form a crimp and secure steering wire 50 within wire mount 48, for example, within wire slot 48A. This process may be performed for each steering wire 50 and each wire mount 48. Additionally, any portion of steering wire 50 that extends proximal to or beyond wire mount 48 may be cut, tied off, or otherwise removed or positioned to not interfere with the movement of main handle body 26A. Furthermore, the crimp that secures each steering wire 50 may be positioned approximately perpendicular to the longitudinal axis of main handle body 26A. Moreover, the crimp that secures each steering wire 50 may be substantially cylindrical and/or free to rotate. In this aspect, as main handle body 26A and ball portion 34 move, the crimp may pivot about its own axis, which may be a different axis than main handle body 26A and ball portion 34. The above-discussed arrangement of the crimp securing steering wire 50 relative to wire mount 48 and ball portion 34 of main handle body 26A may help to reduce, limit, or otherwise mitigate risks of steering wire 50 kinking or otherwise deforming as handle body 26A and ball portion 34 move.

FIG. 3C is a cross-sectional view of ball portion 34 and a portion of main handle body 26A. As shown, ball portion 34 includes a generally spherical outer surface, which helps allow for ball portion 34 to move within socket body 26B. FIG. 3C also illustrates wire mounts 48, each including wire slot 48A. Furthermore, ball portion 34 includes a central opening 34A, for example, to accommodate a conductive element, for example, actuation wire 52. Central opening 34A may widen from a proximal portion to a distal portion, for example, in a triangular or conical shape. In this aspect, actuation wire 52 may extend through central opening 34A, and actuation wire 52 may not contact ball portion 34 regardless of the position of main handle body 26A relative to socket body 26B. Moreover, ball portion 34 may include one or more coupling holes 34B, for example, to couple two halves of main handle body 26A.

FIG. 3D illustrates a portion of medical device handle 26 in a first deflected position. As shown, main handle body 26A is positioned at a non-parallel angle relative to socket body 26B. For example, main handle body 26A is pivoted upward relative to socket body 26B. In this aspect, one control wire, for example, steering wire 50A, which is coupled to a bottom portion of ball portion 34 (as shown), is retracted proximally. As discussed below, proximal retraction of one of steering wires 50 via the movement of main handle body 26A relative to socket body 26B deflects a distal portion of medical device shaft 28. Nevertheless, because actuation wire 52 extends from a central portion of main handle body 26A, the movement of main handle body 26A relative to socket body 26B does not affect the position or movement of actuation wire 52. Instead, the movement of movable body 40 controls the position and movement of actuation wire 52.

Furthermore, as mentioned above, socket body 26B includes ledge 44A to help retain ball portion 34 within socket body 26B. For example, ledge 44A may extend inward around a proximal end of socket body 26B, adjacent to cavity 44. Portions of socket body 26B may be coupled via screws, pins, or other coupling mechanisms being positioned within coupling holes 44C.

It is noted that, although four steering wires 50 and four wire mounts 48 are discussed herein, this disclosure is not so limited. For example, medical device 14 may include two steering wires 50 and two wire mounts 48, three steering wires 50 and three wire mounts 48, five steering wires 50 and five wire mounts 48, etc. Furthermore, wire mounts 48 may be evenly positioned around a circumference of ball portion 34, or, although not shown, wire mounts 48 may be unevenly positioned around the circumference of ball portion 34 or may be located more proximal or more distal on ball portion 34.

Figure 4A:
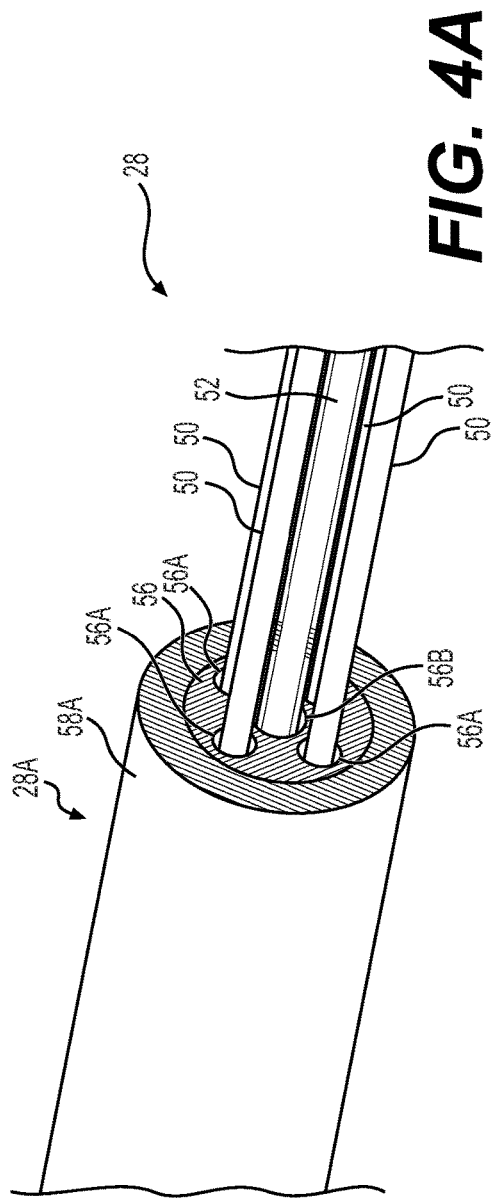
FIGS. 4A and 4B illustrate various cutaway views of the medical device shaft, according to aspects of this disclosure.
Figure 4B:
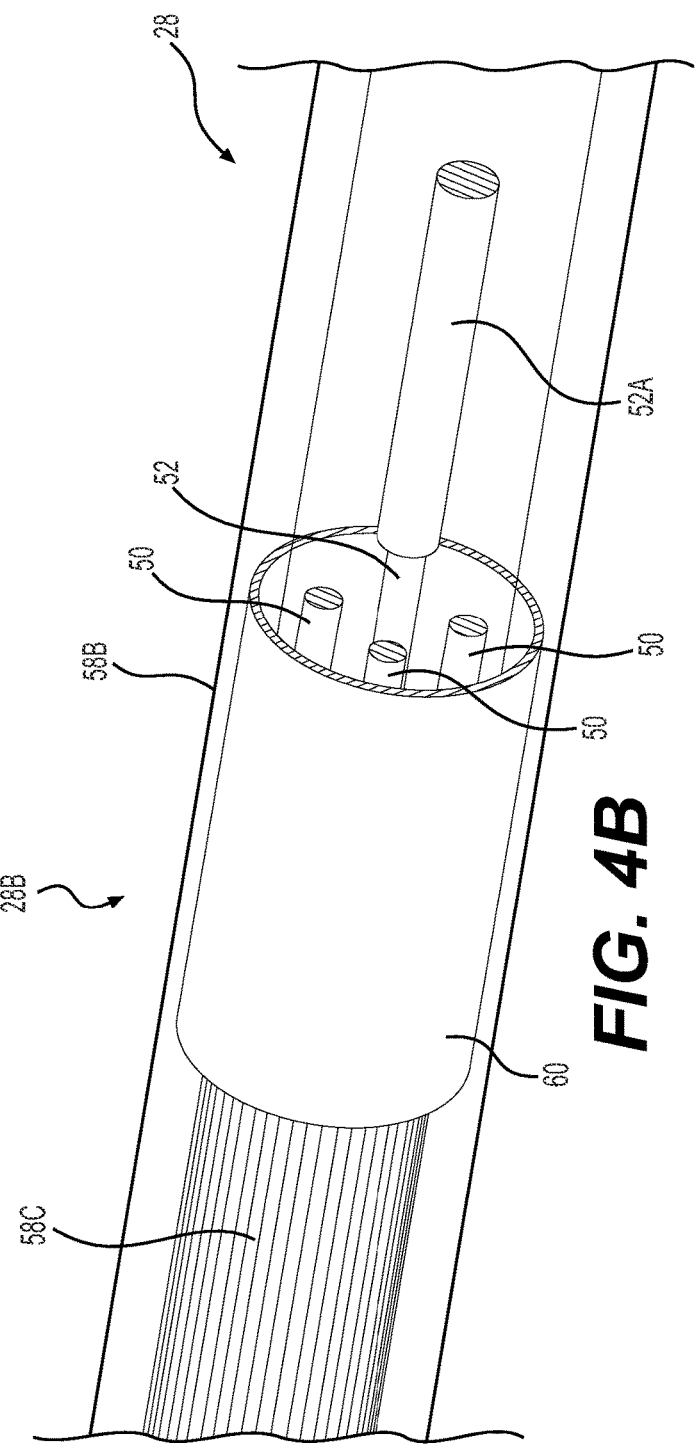

FIGS. 4A and 4B illustrate various details of medical device shaft 28. For example, FIG. 4A illustrates a lateral cross-section of medical device shaft 28 in a main portion 28A of medical device shaft 28, and FIG. 4B illustrates various portions of a distal portion 28B of medical device shaft 28.

As shown in FIG. 4A, main portion 28A of medical device shaft 28 may be formed of an interior multi-lumen element 56, which may be formed of polytetrafluoroethylene ("PTFE") or other appropriate material, for example, via extrusion or other appropriate formation process. Steering wires 50 may be movably positioned within respective lumens 56A in multi-lumen element 56, for example, spaced approximately 90 degrees apart in the cross-section of multi-lumen element 56. Additionally, multi-lumen element 56 may include a central lumen 56B, for example, centrally located in multi-lumen element 56, and actuation wire 52 may be moveably positioned within central lumen 56B. It is noted that, if medical device 14 includes a different number of steering wires, then multi-lumen element 56 may include a different number and/or different spacing of lumens 56A such that each steering wire 50 is housed within a separate lumen of multi-lumen element 56. Additionally, main portion 28A of medical device shaft 28 may include one or more outer sheaths 58A, for example, formed of a polyether block amide ("PEBA") or other appropriate material. Outer sheath (s) 58A may be formed, for example, of PEBA may include a durometer between approximately 60 to 80, for example, approximately 72. Additionally, medical device shaft 28 may include one or more layers of braiding, for example, positioned between multi-lumen element 56 and the one or more outer sheaths 58A. Main portion 28A may span a majority of the length of medical device shaft 28, for example, approximately 70%, approximately 75%, approximately 80%, approximately 85%, approximately 90%, approximately 95%, or more of the length of medical device shaft 28.

Moreover, as shown in FIG. 4B, medical device shaft 28 may include a distal portion 28B with a different arrangement and/or different properties than that shown in FIG. 4A. For example, distal portion 28B may include lumens for steering wires 50 and actuation wire 52, but may include a multi-lumen element (not shown) with more flexibility, for example, formed of PEBA, for example, with a durometer between approximately 25 to 55, for example between approximately 33 to 50. Additionally, distal portion 28B may include an outer sheath 58B, for example, formed of PEBA, with a durometer between approximately 20 to 50, for example, approximately 33. Distal portion 28B may also include one or more layers of braiding 58C, for example, positioned between the multi-lumen element and the one or more outer sheaths 58B. In these aspects, distal portion 28B of medical device shaft 28 may be more flexible than main portion 28A, for example, for distal portion 28B to be deflected by movement of steering wires 50.

FIG. 4B also illustrates various features that may be incorporated at a distal portion 28B of medical device shaft 28 in order to steer or deflect distal portion 28B. For example, distal ends of each of steering wires 50 may be welded, adhered, or otherwise fixedly coupled to a ring 60. Ring 60 may be substantially cylindrical and positioned radially outside of or around steering wires 50. Ring 60 may be formed of steel or another appropriate metal or other material. Additionally, a distal portion 52A of actuation wire 52 may be connected (directly or indirectly) to electrode 38 (FIG. 1) to control the extension or retraction of electrode 38. For example, distal portion 52A may include a widened extension portion. Additionally, as discussed above, energy delivered through hub 36B on medical device handle 26 may be delivered to electrode 38 via actuation wire 52.

Figure 5:
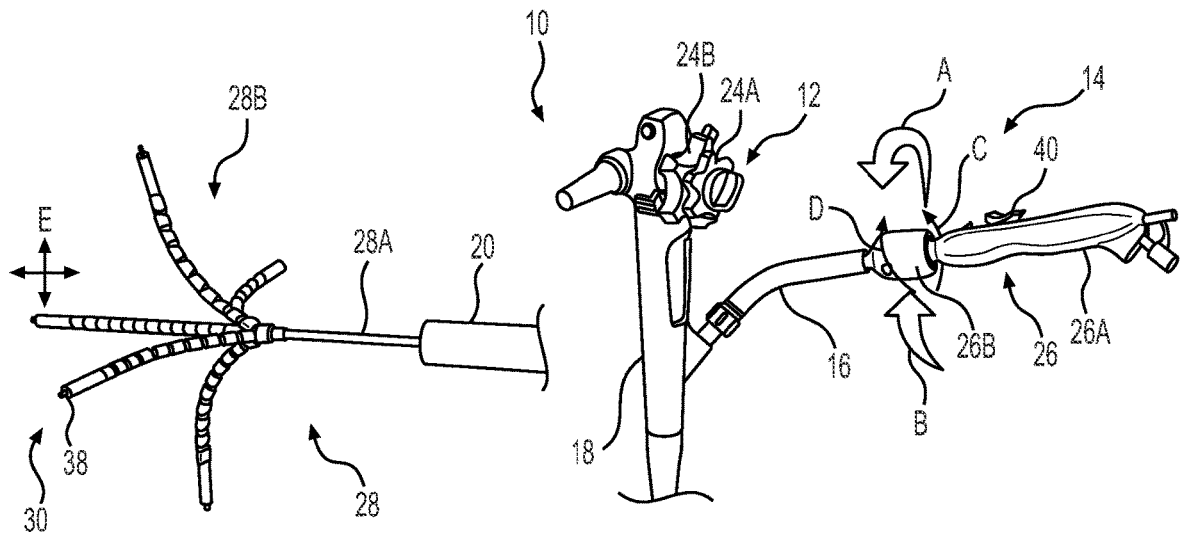
FIG. 5 illustrates the medical system with the medical device handle and a distal portion of the medical device shaft in various configurations, according to aspects of this disclosure.

FIG. 5 illustrates various configurations of system 10 and the different positions of medical device shaft 28. As shown, medical device 14 is coupled to handle 18 of insertion device 12 via adapter 16. Additionally, medical device shaft 28 is extended through insertion device shaft 20. Main handle body 26A may be pivoted in any direction relative to socket body 26B, indicated by arrows A, B, C, and D. For example, the user may hold insertion device handle 18 with one hand, and may hold medical device handle 26 in another hand. The user may then move his or her wrist of the another hand in order to control main handle body 26A. In this aspect, main portion 28A of medical device shaft 28 may remain stationary, but distal end portion 28B of medical device shaft 28 may be deflected in any direction, indicated by arrows E. For example, moving the user's wrist left or right will deflect distal end 30 of medical device shaft 28 right or left. Similarly, moving the user's wrist up or down, or side to side, will deflect distal end 30 of medical device shaft 28 down or up, or side to side.

In one or more aspects, a right-side steering wire 50 may be coupled to a right side of ball portion 34 of main handle body 26A. The right-side steering wire 50 may pass through the right-side lumen of multi-lumen element 56, and the right-side steering wire 50 may then be coupled to a right-side portion of distal end 20A of insertion device shaft 20. A left-side steering wire 50 may be coupled to a left side of ball portion 34 of main handle body 26A. The left-side steering wire 50 may pass through the left-side lumen of multi-lumen element 56, and the left-side steering wire 50 may then be coupled to a left-side portion of distal end 20A of insertion device shaft 20. Accordingly, moving main handle body 26A to the right may cause the left-side steering wire 50 to be under tension, causing distal end 20A of insertion device shaft 20 to bend or deflect to the left. Similarly, moving main handle body 26A to the left may cause the right-side steering wire 50 to be under tension, causing distal end 20A of insertion device shaft 20 to bend or deflect to the right. In another aspect, the right-side steering wire 50 may be coupled to the right side of ball portion 34 of main handle body 26A, and the left-side steering wire 50 may be coupled to the left side of ball portion 34 of main handle body 26A. The right-side steering wire 50 may pass through the left-side lumen of multi-lumen element 56, and the right-side steering wire 50 may then be coupled to a left-side portion of distal end 20A of insertion device shaft 20. Likewise, the left-side steering wire 50 may pass through the right-side lumen of multi-lumen element 56, and the left-side steering wire 50 may then be coupled to a right-side portion of distal end 20A of insertion device shaft 20. In this aspect, moving main handle body 26A to the right may cause the right-side steering wire 50 to be under tension, causing distal end 20A of insertion device shaft 20 to bend or deflect to the right. Similarly, moving main handle body 26A to the left may cause the left-side steering wire 50 to be under tension, causing distal end 20A of insertion device shaft 20 to bend or deflect to the left.

Insertion device shaft 20 may also be deflected, for example, via knobs 24A, 24B. Furthermore, although not shown, medical device handle 26 may be retracted proximally relative to adapter 16 and handle 18 of insertion device 12 to retract medical device shaft 28 relative to insertion device shaft 20, for example, to retract distal end 30 of medical device shaft 28. Additionally, the user may extend or retract electrode 38 from distal end 30 of medical device shaft 28 via movable body 40, for example, via action from the user's thumb.

Figure 6A:
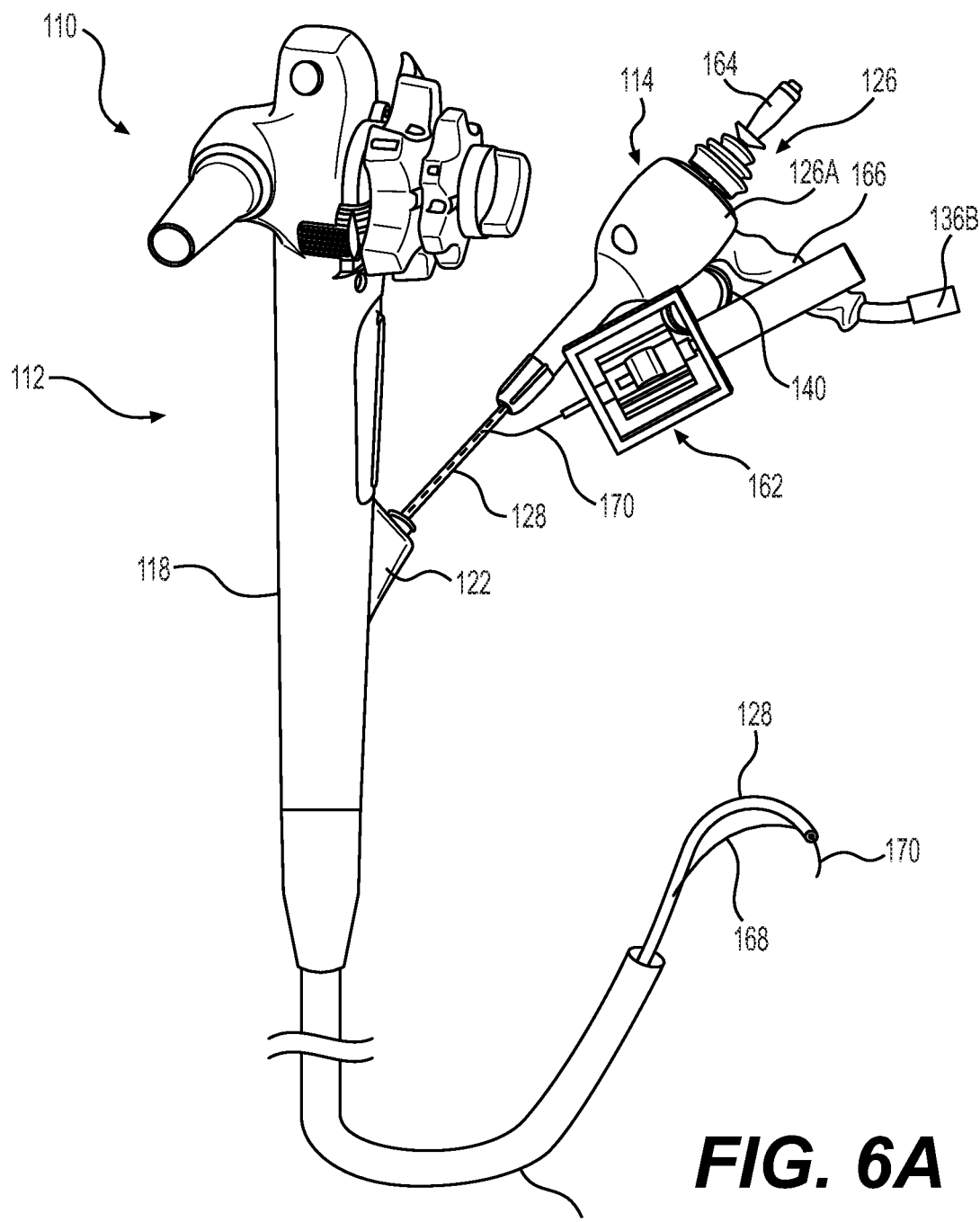
FIGS. 6A and 6B illustrate another medical device system including an insertion device, a medical device, and a guide wire device, where the medical device includes a medical device handle, a medical device shaft, and a distal end, according to aspects of this disclosure.
Figure 6B:
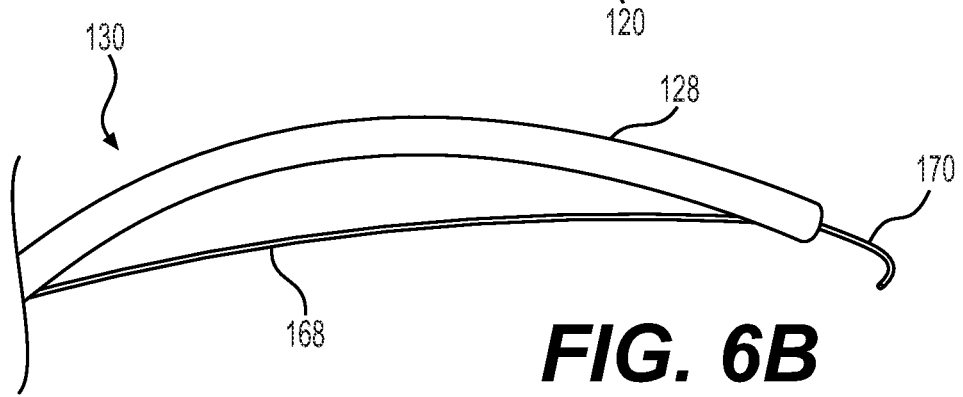

FIGS. 6A and 6B illustrate another exemplary medical system 110. As shown, medical system 110 includes an insertion device 112, for example, similar to insertion device 12. Medical system 110 also includes a medical device 114. In some aspects, medical system 110 does not include an adapter. Furthermore, medical system 110 may include a guide wire device 162. Medical device 114 may be coupled to and/or delivered to a treatment site through a handle 118 and shaft 120 of insertion device 112, as discussed above. Guide wire device 162 may be coupled to medical device 112, for example, via a slot or opening in a portion of medical device shaft 128 or medical device handle 126.

Medical device 114 includes a medical device handle 126 and a medical device shaft 128. Medical device handle 126 may include a stationary handle portion or a handle body 126A, a movable handle portion or a joystick 164 coupled to handle body 126A via a ball-socket coupling, and a movable body 140. Additionally, medical device handle 126 may include a handle extension 166, for example, to be gripped by a user. Handle extension 166 may include a hub 136B, for example, to couple an energy source to medical device 114. Although not shown, medical device 114 may include one or more ports, for example, to couple a fluid source to medical device 114. Medical device shaft 128 may be delivered through a port 122 in a handle 118 of insertion device 112, as discussed above, and may be moveable proximally and distally to control the location of a distal end 130 of medical device shaft 128. Moreover, joystick 164 may be movable to deflect distal end 130 of medical device shaft 128, and movable body 140 may be movable (e.g., via a user's finger) to control the position of the portion of distal end 130 of medical device shaft 128. In these aspects, medical device 114 may be a sphincterotome or other appropriate medical device.

As shown in FIGS. 6A and 6B, distal end 130 of medical device shaft 128 may include a cautery wire 168, for example, extending between a first portion of medical device shaft 128 and a second portion of medical device shaft 128. For example, movement of movable body 140 may distally extend or proximally retract cautery wire 168, for example, to control the shape or position of distal end 130 of medical device shaft 128. Additionally, a guide wire 170 may extend through medical device shaft 128. Guide wire device 162 may control the position of guide wire 170, and thus also, in some aspects, may control the position of distal end 130 of medical device shaft 128.

Figure 7:
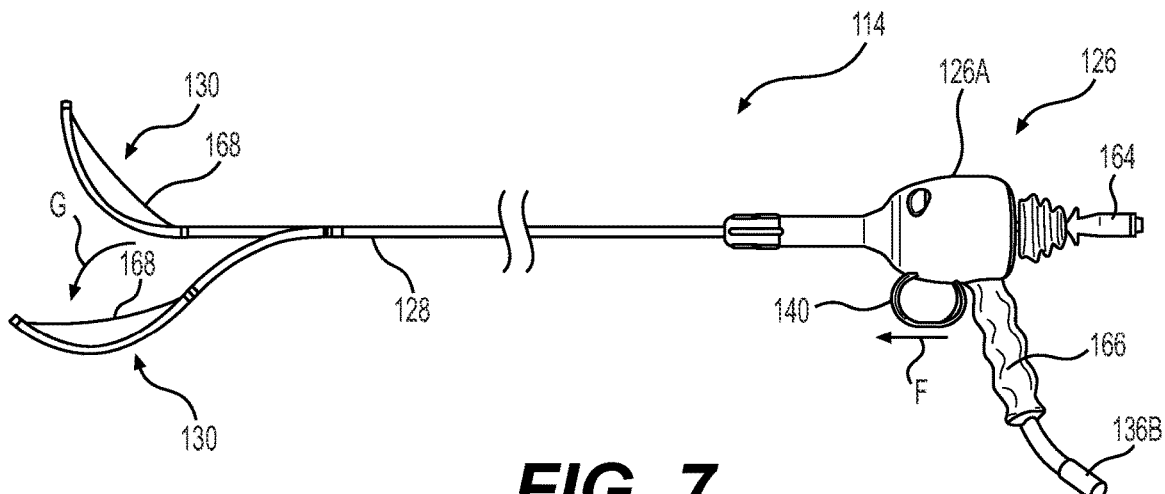
FIG. 7 illustrates the medical device, with the medical device handle and the medical device shaft in various configurations, according to aspects of this disclosure.

FIG. 7 illustrates the movement of movable body 140 and the movement of cautery wire 168 in order to control the shape or position of distal end 130 of medical device shaft 128. It is noted that medical device 114 is shown in FIG. 7 uncoupled from insertion device 112, but that the movements disclosed may be performed with medical device 114 coupled to insertion device 112. As shown, medical device 114 includes movable body 140 that is movable relative to a main handle body 126A. Moveable body 140 may include a ring, for example, to receive a user's finger. In this aspect, the user may grasp handle extension 166 with one hand, and also manipulate movable body 140 with a finger (e.g., a forefinger) of the same one hand. Moveable body 140 may be distally extended, for example, in the direction of arrow F, and distal end 130 may move from a first configuration (e.g., a bent configuration) to a second configuration (e.g., an extended configuration), for example, in the direction of arrow G. Similarly, movable body 140 may be proximally retracted, and distal end 130 of medical device shaft 128 may move from the second configuration to the first configuration. Additionally, there may be one or more intermediate configurations based on the intermediate positions of movable body 140.

As discussed above with respect to main handle body 26A and socket body 26B, joystick 164 may be movable relative to main handle body 126A to further manipulate distal end 130 of medical device shaft 128. For example, joystick 164 and main handle body 126A may form a ball and socket assembly with a plurality of steering wires, as discussed above. Additionally, joystick 164 may be coupled to a proximal portion of main handle body 126A.

Figure 8A:
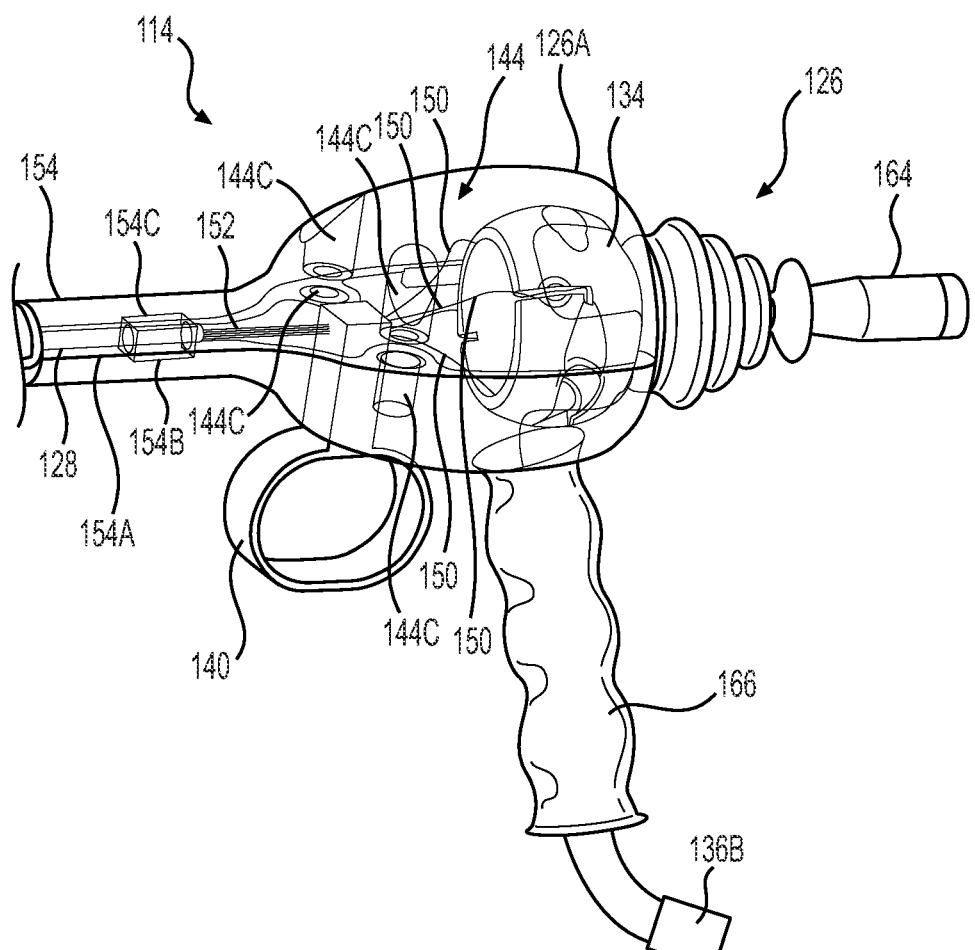
FIGS. 8A and 8B illustrate various aspects of the medical device handle and medical device shaft, according to aspects of this disclosure.
Figure 8B:
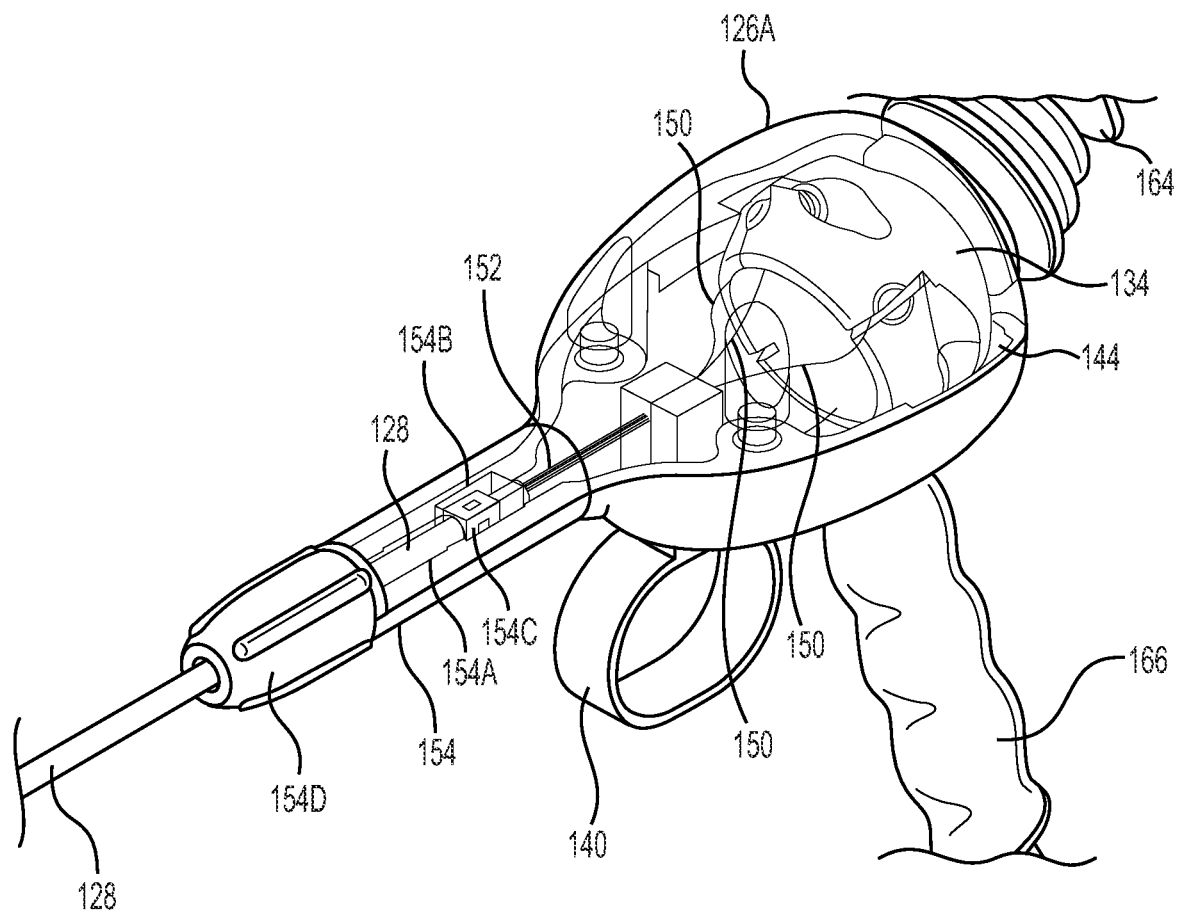

FIGS. 8A and 8B illustrate portions of medical device handle 126, with main handle body 126A as being transparent. As shown, joystick 164 may be coupled to a ball portion 134, and ball portion 134 may be received within a cavity 144 in a proximal portion of main handle body 126A. In this aspect, a distal portion of joystick 164 may be integrally formed with a proximal portion of ball portion 134. Alternatively, the distal portion of joystick 164 may be coupled to the proximal end of ball portion 134, for example, via an adhesive, one or more screws, a snap fit, or other appropriate coupling. Accordingly, movement of joystick 164 also moves ball portion 134, for example, within cavity 144. A plurality of steering wires 150 may be coupled to portions of ball portion 134, and steering wires 150 may be coupled to one or more distal portions of medical device shaft 128, as discussed above, in order for manipulation of joystick 164 to control the deflection or movement of a distal portion of medical device shaft 128.

Moreover, movable body 140 may be coupled to an actuation wire 152, such that movement of movable body 140 relative to main handle body 126A controls the position of distal end 130 of medical device shaft 128. Although not shown, main handle body 126A may include a slot in which movable body 140 may move proximally and/or distally. Steering wires 150 and actuation wire 152 may extend through medical device shaft 128, for example, through one or more lumens, as discussed above. Additionally, steering wires 150 may be routed around the movable body 140. Furthermore, as shown in FIG. 8A, main handle body 126A may be formed, for example, of two halves, and main handle body 126A may include one or more coupling holes 144C, and the halves may be coupled around ball portion 134 and other components, for example, via one or more screws, bolts, etc. positioned within coupling holes 144C.

Main handle body 126A may include a cylindrical portion 154 with a channel 154A to receive a portion of medical device shaft 128. Although referred to as a cylindrical portion herein, it is contemplated that portion 154 may have any suitable cross-sectional shape and may be, for example, tapered. Additionally, channel 154A may include a widened channel portion or slot 154B. In some aspects, channel 154A may be generally cylindrical, and slot 154B may be generally rectangular, although other shapes are contemplated. As shown in FIG. 8B, a crimp 154C may be positioned around a portion of medical device shaft 128 within slot 154B, for example, to help couple medical device shaft 128 to medical device handle 126. Furthermore, although not shown, one or more additional wires or conduits may couple hub 136B to actuation wire 152 (e.g., passing through handle extension 166 and a portion of main handle body 126A), for example, to deliver energy to actuation wire 152. As shown in FIG. 8B, a handle cap 154D may be coupled to a distal portion of cylindrical portion 154 to help couple portions of main handle body 126A and to help couple medical device shaft 128 to main handle body 126A.

Figure 9:
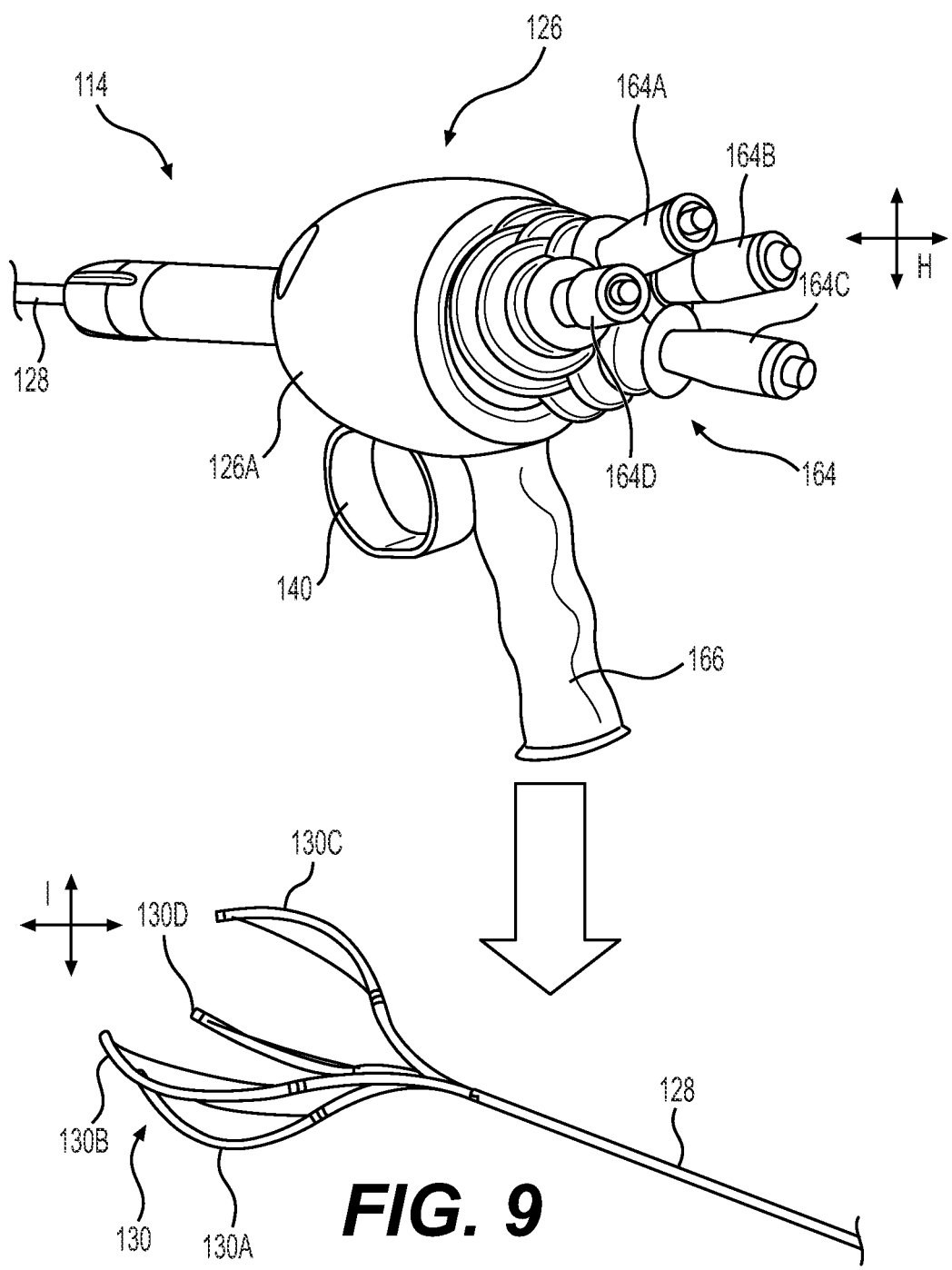
FIG. 9 illustrates the medical device handle and the medical device shaft in various configurations, according to aspects of this disclosure.

FIG. 9 illustrates the movement of medical device 114. Specifically, FIG. 9 illustrates the movement of joystick 164 relative to main handle body 126A and the movement of distal end 130 of medical device shaft 128. Joystick 164 may be positioned in various positions, for example, 164A, 164B, 164C, and 164D, or other intermediate positions. Joystick 164 may be manipulated by one or more of the user's fingers, for example, by the user's thumb, by the user's thumb and forefinger, etc. In one aspect, the user may grasp handle extension 166 with one hand and manipulate joystick 164 with a thumb of the same one hand. As a result, distal end 130 may be deflected to various positions, for example, 130A, 130B, 130C, 130D, or various intermediate positions, which correspond to the various joystick positions. Additionally, it is noted that joystick 164 may move in any direction, indicated by arrows H, which may deflect distal end 130 in any direction, indicated by arrows I. Furthermore, joystick 164 may move incrementally and to different extents in the various directions, for example, to deflect distal end 130 in a semi-spherical range, for example, relative to a distal end of insertion device 112. In some aspects, depending on the deflectability of distal end 130, movement of joystick 164 may deflect distal end 130 in a range that is larger than a semi-spherical range. Although not shown in FIG. 9, movement or deflection of insertion device shaft 120 and/or movable body 140 may also control the movement of distal end 130, as discussed above. Furthermore, medical device 114 may be moved proximally or distally relative to insertion device 112 (e.g., relative to port 122) to control the position of distal end 130 relative to the distal end of insertion device shaft 120.

Figure 10A:
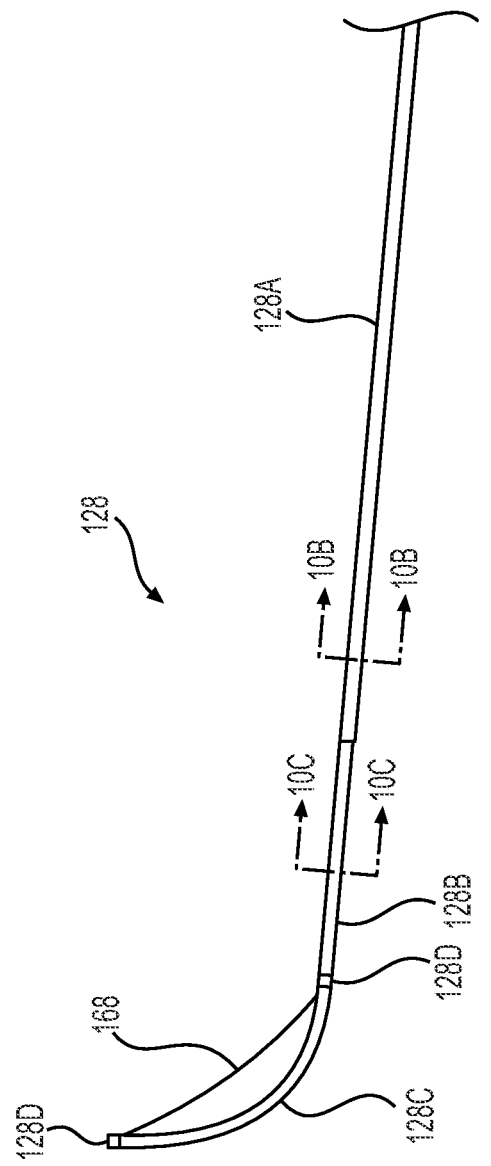
FIGS. 10A-10D illustrate various views of the medical device shaft, including cross-sections along various portions of the medical device shaft, according to aspects of this disclosure.

FIGS. 10A-10D illustrate various features that may be incorporated in medical device shaft 128. As shown in FIG. 10A, medical device shaft 128 may include a plurality of sections. For example, medical device shaft 128 may include a main portion 128A. Main portion 128A may span a majority of the length of medical device shaft 28, for example, approximately 70%, approximately 75%, approximately 80%, approximately 85%, approximately 90%, approximately 95%, or more of the length of medical device shaft 128. Additionally, medical device shaft 128 may include a distal shaft portion 128B and a distal cautery shaft portion 128C. Distal shaft portion 128B may be positioned between main portion 128A and distal cautery shaft portion 128C. Moreover, distal cautery shaft portion 128C may include one or more support portions 128D, which may help to support cautery wire 168, for example, as cautery wire 168 extends from distal cautery shaft portion 128C. As mentioned, cautery wire 168 may extend from openings in distal cautery shaft portion 128C. Furthermore, as discussed above, the different portions of medical device shaft 128 may have different properties, layers of material, etc., which may affect the flexibility or rigidity of the various portions.

Figure 10B:
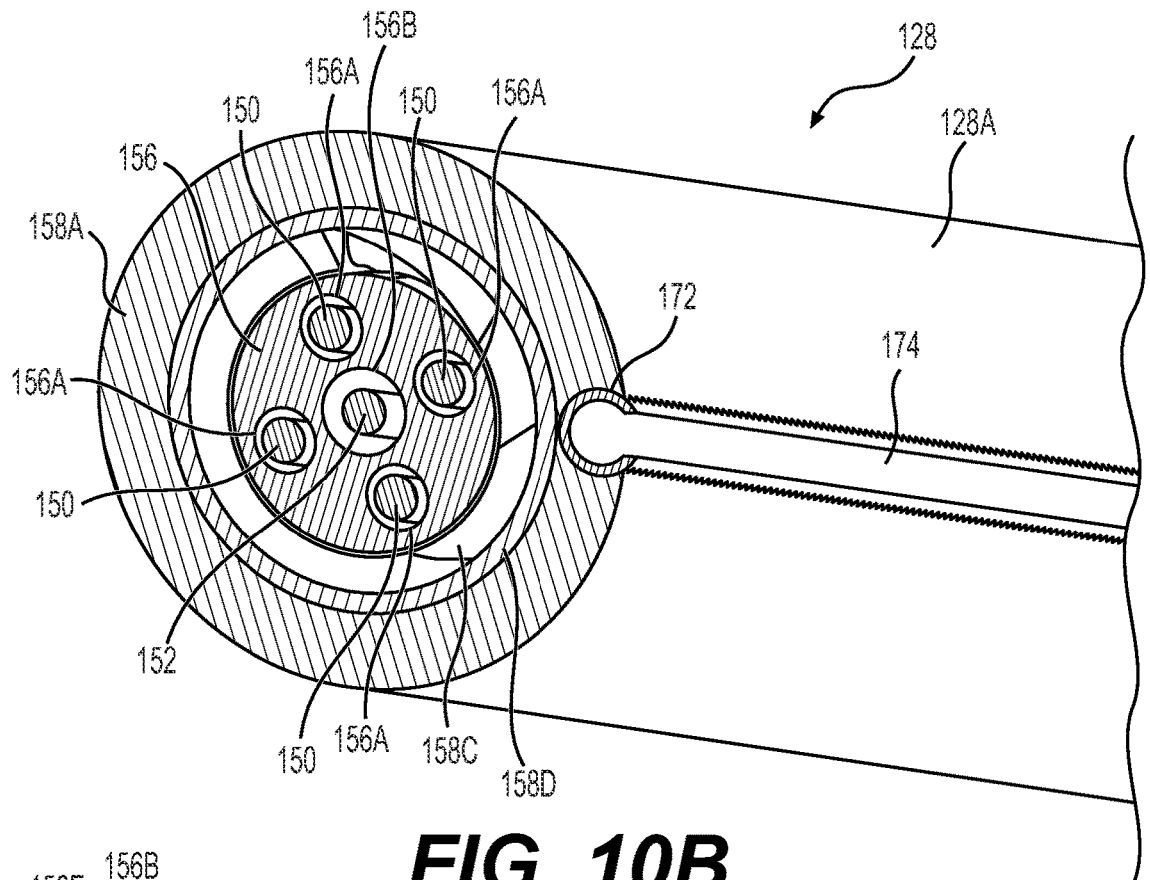

FIG. 10B illustrates a perspective view of a lateral cross-section of main portion 128A of medical device shaft 128, indicated by the line 10B-10B in FIG. 10A. As shown in FIG. 10B, main portion 128A of medical device shaft 128 includes an interior multi-lumen element 156, which may be formed of polytetrafluoroethylene ("PTFE") or other appropriate material, for example, via extrusion or other appropriate formation process. Multi-lumen element 156 may include a durometer between approximately 20 to 60, for example, between approximately 33 and 50. Steering wires 150 may be movably positioned within respective lumens 156A in multi-lumen element 156, for example, spaced approximately 90 degrees apart in the cross-section of multi-lumen element 156. Additionally, multi-lumen element 156 may include a central lumen 156B, for example, centrally located in multi-lumen element 156, and actuation wire 152 may be moveably positioned within central lumen 156B.

Main portion 128A of medical device shaft 128 may include one or more outer sheaths 158A, for example, formed of a polyether block amide ("PEBA") or other appropriate material. In this aspect, a braiding 158C and one or more sheaths 158D (e.g., formed of PEBA with a durometer of approximately 60 to 80, for example, approximately 72) may be positioned between multi-lumen element 156 and outer sheath 158A. Outer sheath 158A may be formed via an extrusion, and may be coupled to the other components of main portion 128A via heat shrinking. As shown, outer sheath 158A may include a C-shaped opening 172, which may receive a C-shaped tube 174. Tube 174 may receive a portion of guide wire 170 (FIGS. 6A and 6B), for example, in order for medical device shaft 128 to be delivered to a treatment site over a guidewire.

Figure 10C:
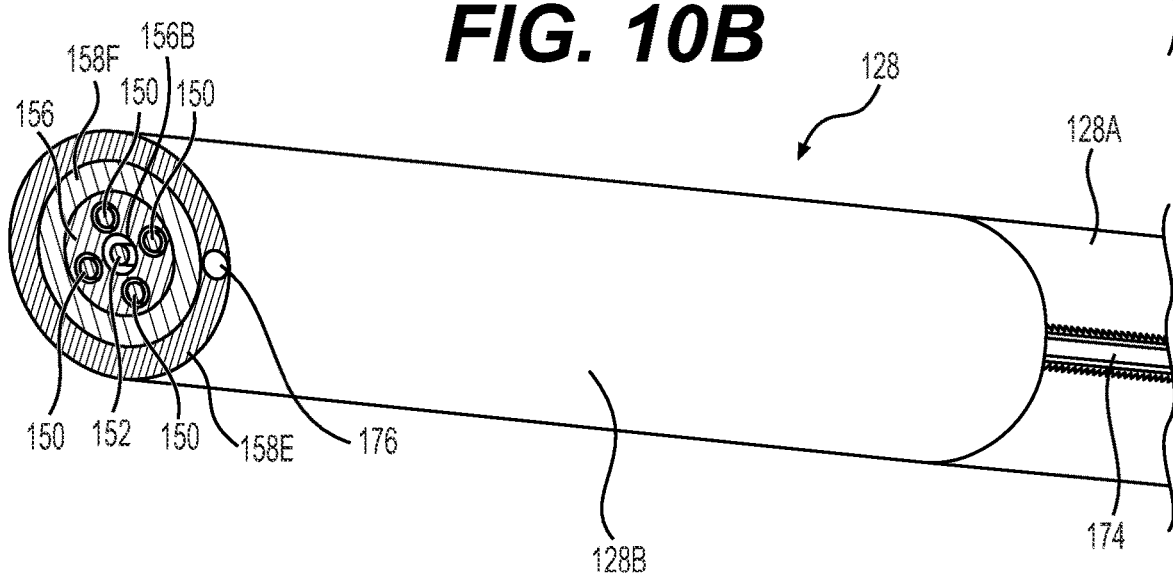

FIG. 10C illustrates a perspective view of a lateral cross-section of distal shaft portion 128B, indicated by the line 10C-10C in FIG. 10A. As shown in FIG. 10C, distal shaft portion 128B may include multi-lumen element 156, which includes respective lumens for wires 150 and actuation wire 152, as discussed above. Distal shaft portion 128B of medical device shaft 128 may include one or more outer sheaths 158E, for example, formed of a polyether block amide ("PEBA") or other appropriate material. In this aspect, a braiding 158F and one or more intermediate sheaths (not shown) may be positioned between multi-lumen element 156 and outer sheath 158E. Braiding 158F and the intermediate sheath(s) may include a durometer between approximately 20 to 60, for example, between approximately 33 to 50. Outer sheath 158E may be formed via an extrusion, and may be coupled to the other components of distal shaft portion 128B via, e.g., heat shrinking. As shown, outer sheath 158E may include an opening 176, which may include a circular cross-section to form a cylindrical opening. Opening 176 may at least partially align with C-shaped tube 174. In this aspect, a guide wire may pass through both distal shaft portion 128B and main portion 128A, with the guide wire being enclosed within a portion of outer sheath 158E over distal shaft portion 128B. For example, a guide wire may be used to deliver medical device shaft 128, and, optionally, insertion device shaft 120, to the treatment site. Furthermore, one or more guide wires may be delivered through and/or removed from medical device shaft 128 in order to treat the treatment site.

Figure 10D:
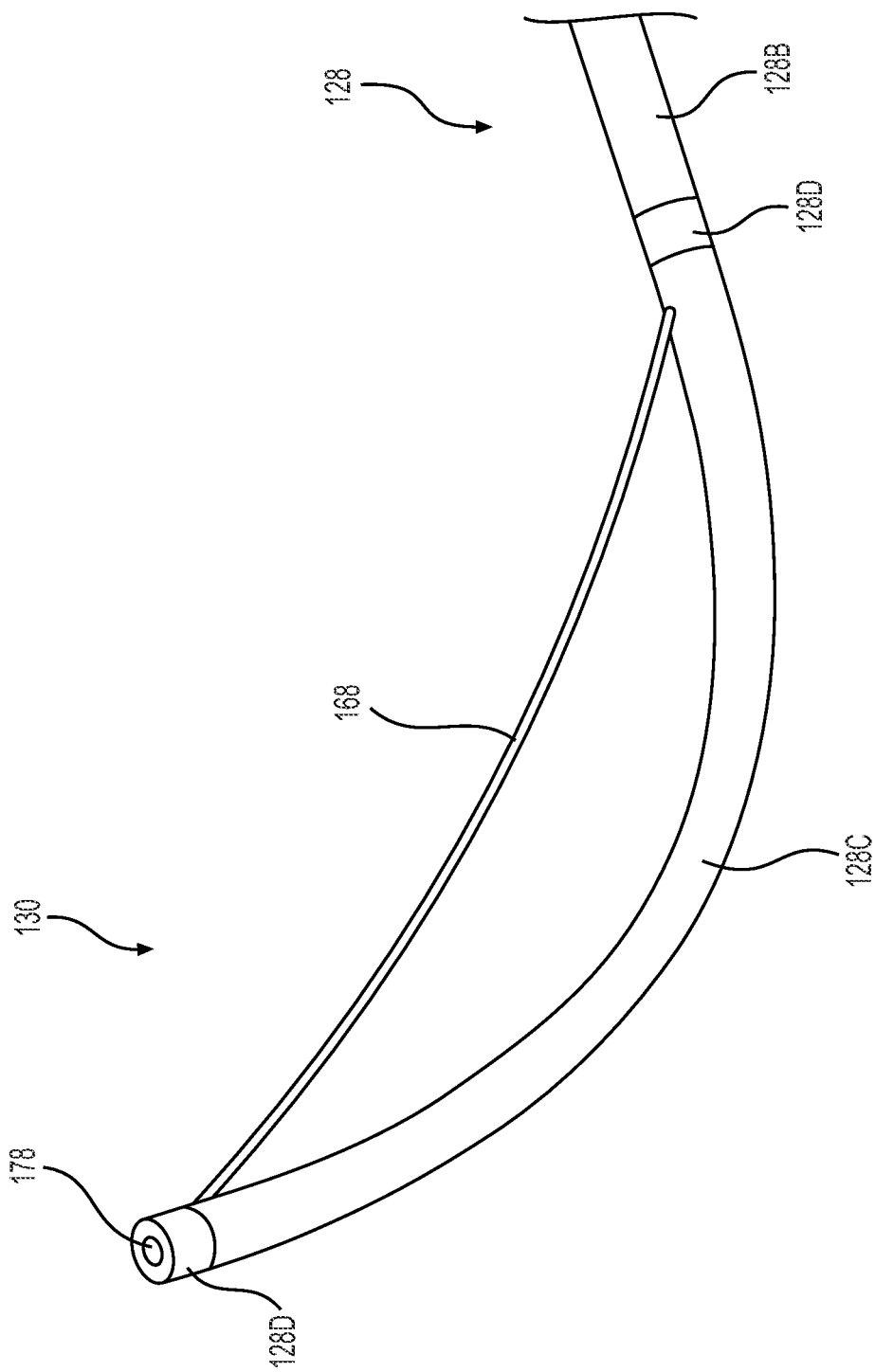

FIG. 10D illustrates distal end 130 of medical device shaft 128, including distal cautery shaft portion 128C extending from distal shaft portion 128B. As mentioned, cautery wire 168 may extend from portions of distal cautery shaft portion 128C. Additionally, distal cautery shaft portion 128C may include a distal opening 178. Although not shown, opening 176 in distal shaft portion 128B may transition from an exterior of medical device shaft 128 to a central portion of medical device shaft 128 over a portion distal cautery shaft portion 128C. In this aspect, a guide wire (not shown) may pass through distal opening 178 in distal cautery shaft portion 128C and into opening 176 in distal shaft portion 128B (FIG. 10C). Furthermore, although not shown, portions of steering wires 150 may be coupled to portions of distal cautery shaft portion 128C, for example, such that movement of joystick 164 moves distal cautery shaft portion 128C, as discussed above, for example, with respect to FIG. 9.

Figure 11A:
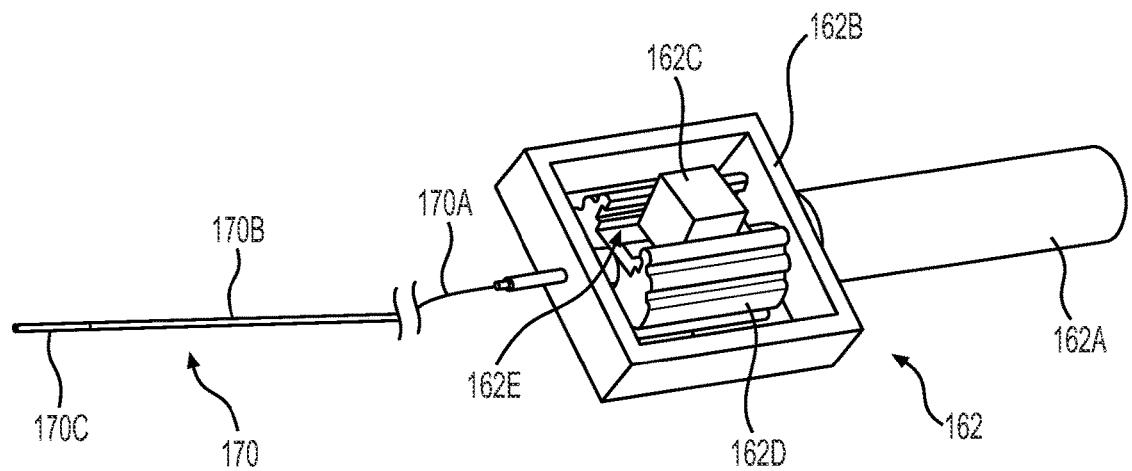
FIG. 11A illustrates a perspective view of the guide wire device of FIG. 7.
Figure 11B:
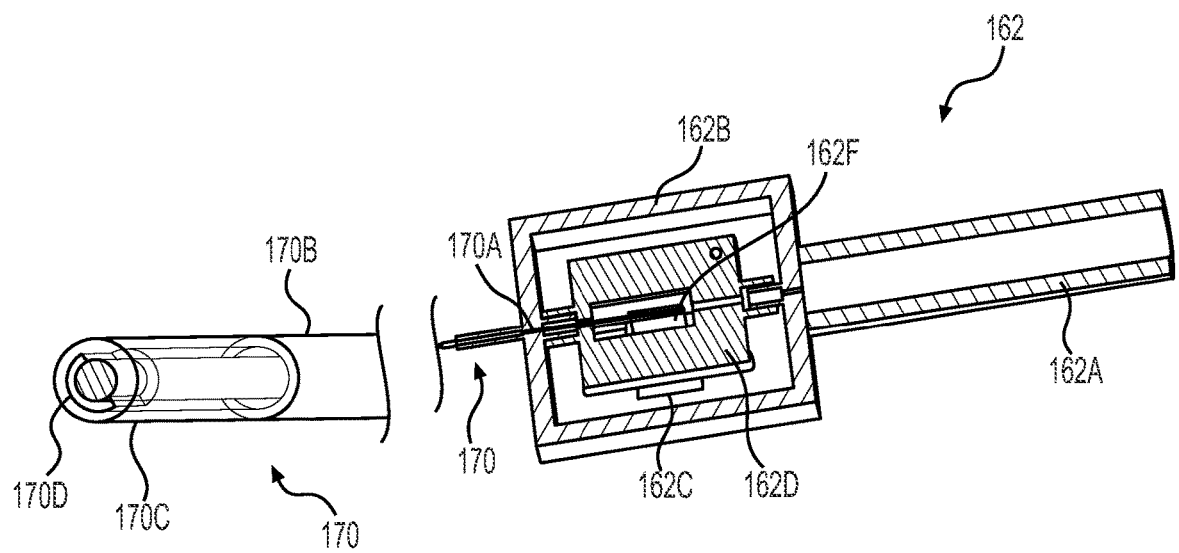
FIG. 11B illustrates a cross-sectional view of the guide wire device of FIG. 7, according to aspects of this disclosure.

FIGS. 11A, 11B, and 12A-12C illustrate various features of guide wire device 162. Guide wire device 162 includes a handle portion 162A and guide wire 170. Handle portion 162A may include a casing 162B, for example, for a user to hold. Handle portion 162A also includes a button 162C and a roller 162D. Button 162C may be positioned within a channel 162E in roller 162D. As shown in FIG. 11B, button 162C may be coupled to a portion of guide wire 170, for example, to a pull wire 170A. In one aspect, a sleeve 162F may be crimped to pull wire 170A, and sleeve 162F may be coupled to button 162C, for example, via an adhesive, one or more screws, a snap fit, or other appropriate coupling. In this aspect, movement of button 162C, for example, within channel 162E, may control the movement, and thus actuation, of pull wire 170A. Additionally, roller 162D may be rotatably coupled to casing 162B, for example, via overlapping extensions, as shown in FIG. 11B. In this aspect, rotating roller 162D may also rotate button 162C, and thus also rotate pull wire 170A. Although not shown, guide wire device 162 may include one or more frictional or locking elements, for example, to limit and/or lock the movement of button 162C and/or roller 162D.

Guide wire 170 may include a main wire portion 170B and a distal wire portion 170C. Main wire portion 170B may be formed of a hollow wire, for example, formed of nitinol or other appropriate material, and may be fixedly coupled to casing 162B. Distal wire portion 170C may be formed of a flexible material, for example, PEBA, rubber, PTFE, etc. Furthermore, pull wire 170A may be a solid wire, for example, formed of nitinol, stainless steel, or other appropriate material. Distal wire portion 170C may articulate, for example, based on the position of pull wire 170A. For example, a distal end of pull wire 170A may be coupled to a distal portion of distal wire portion 170C, for example via an adhesive, heat shrinking, crimping, or other appropriate coupling.

FIG. 11B shows distal wire portion 170C as being partially transparent. Distal wire portion 170C may include a closed distal end. In this aspect, a coupling 170D between a portion of pull wire 170A and distal wire portion 170C may only be formed over a circumferential portion of pull wire 170A. In this aspect, less than an entire circumference of the portion of pull wire 170A that is positioned within distal wire portion 170C may form coupling 170D. For example, a semi-circular or quarter-circular portion of the outer circumference of pull wire 170A may be coupled to an interior of distal wire portion 170C at coupling 170D. In this aspect, movement of pull wire 170A, for example, via button 162C and/or roller 162D, may articulate distal wire portion 170C. Furthermore, if distal wire portion 170C is positioned within a portion of medical device shaft 128, for example, distal cautery shaft portion 128C and/or distal shaft portion 128B, then movement of distal wire portion 170C may also articulate the portion of medical device shaft 128.

Figure 12A:
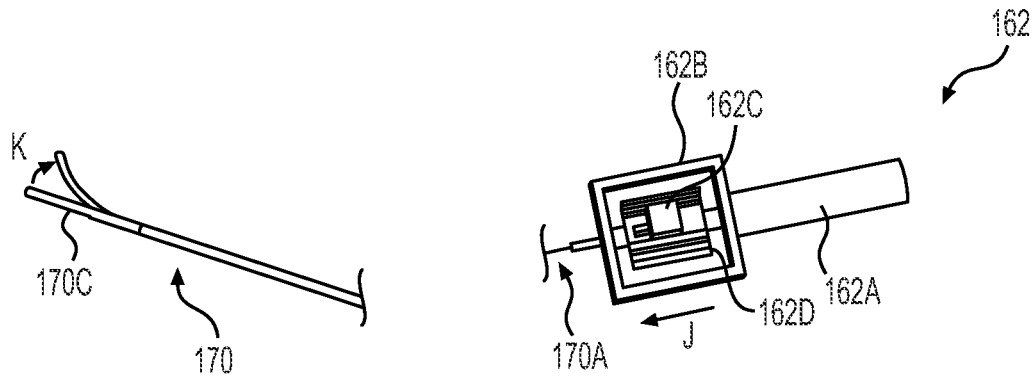
FIGS. 12A-12C illustrate portions of the guide wire device, including a handle portion and a distal end of a guide wire shaft, according to aspects of this disclosure.
Figure 12B:
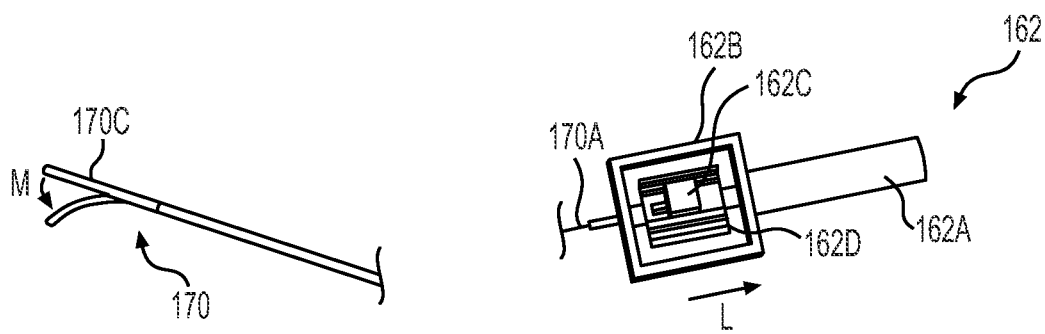
Figure 12C:
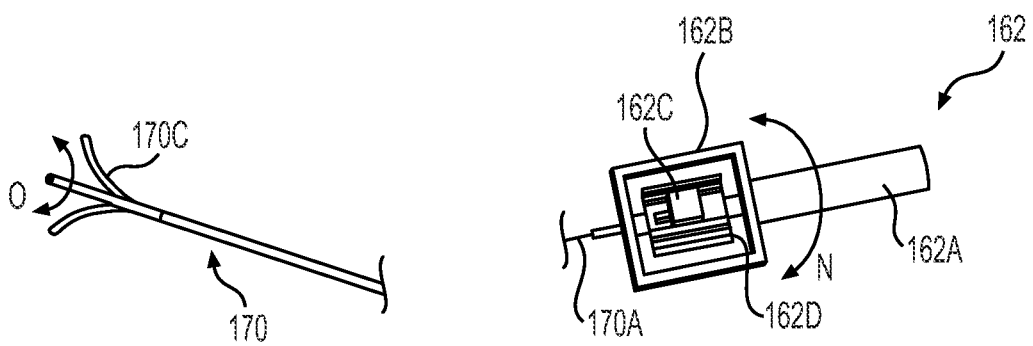

FIGS. 12A-12C illustrate various movements of handle portion 162A and guide wire 170. For example, FIG. 12A illustrates button 162C being actuated distally (i.e., in the direction of arrow J) within channel 162E in roller 162D. In this aspect, distal articulation of button 162C articulates pull wire 170A distally. Based on the connection of pull wire 170A to distal wire portion 170C, the distal articulation of pull wire 170A articulates distal wire portion 170C in a first direction, for example, upward (i.e., in the direction of arrow K).

FIG. 12B illustrates button 162C being actuated proximally (i.e., in the direction of arrow L) within channel 162E in roller 162D. In this aspect, proximal articulation of button 162C articulates pull wire 170A proximally. Based on the connection of pull wire 170A to distal wire portion 170C, the proximal articulation of pull wire 170A articulates distal wire portion 170C in a second direction, for example, downward (i.e., in the direction of arrow M).

Furthermore, FIG. 12C illustrates roller 162D, and thus button 162C, being rotated clockwise or counterclockwise (i.e., in the direction of arrows N) relative to casing 162B. In this aspect, rotation of button 162C rotates pull wire 170A. Furthermore, button 162C may be articulated, for example, either proximally or distally, as discussed above, and pull wire 170A and distal wire portion 170C may be rotated and articulated in a plurality of directions (i.e., in the direction of arrows O). In this aspects, and as discussed above, guide wire 170 may help to guide and/or articulate a portion of medical device shaft 128.

Figure 13:
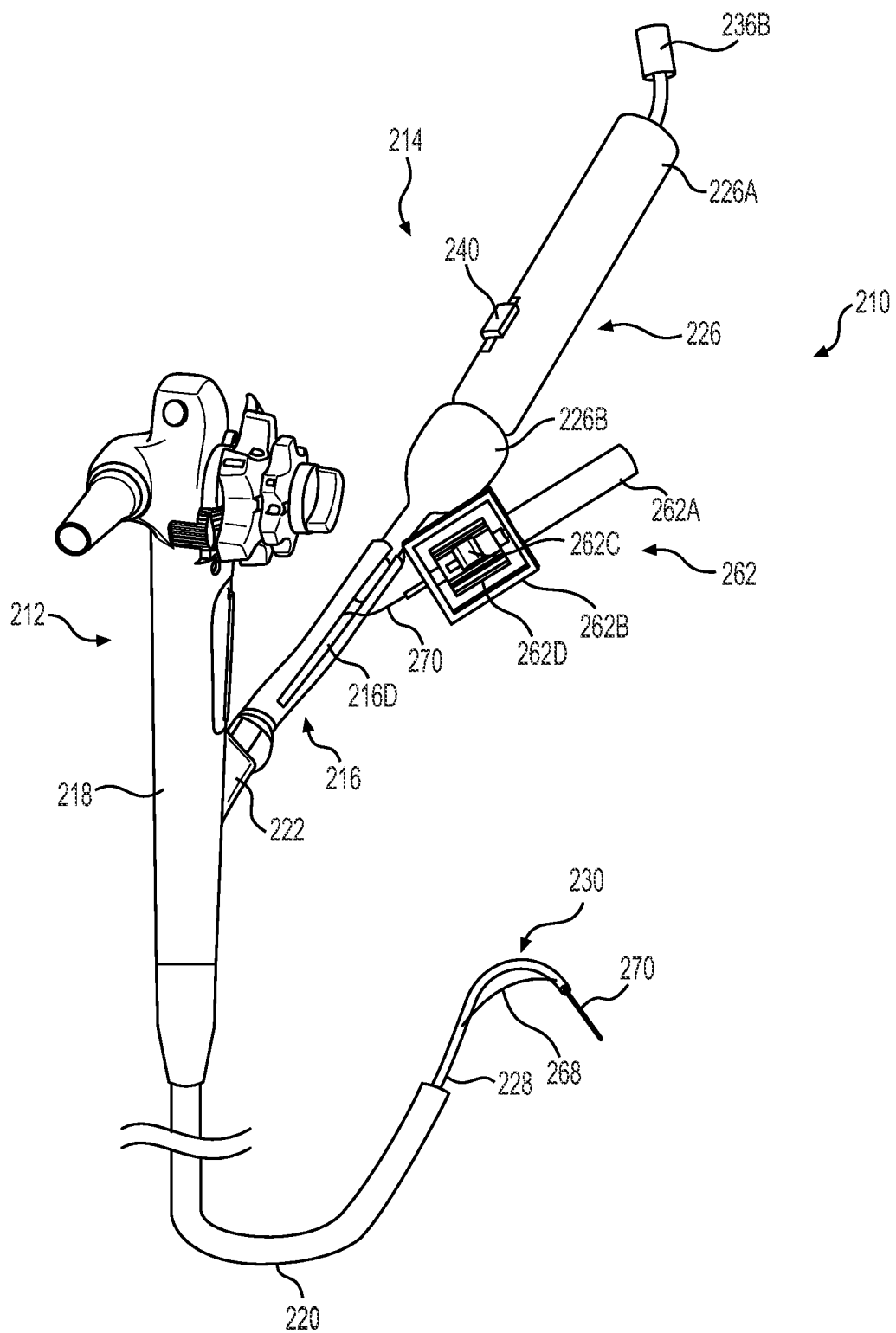
FIG. 13 illustrates another medical device system including an insertion device, a medical device, and a guide wire device, according to aspects of this disclosure.

FIG. 13 illustrates another exemplary medical system 210, according to aspects of this disclosure. System 210 includes an insertion device 212, for example, similar to insertion device 12. Medical system 210 also includes a medical device 214. Medical system 210 may include an adapter 216, for example, coupling medical device 214 to a port 222 of insertion device 212. Furthermore, medical system 210 may include a guide wire device 262, for example, similar to guide wire device 162, and a cautery wire 268, for example, similar to cautery wire 168. Medical device 214 may be coupled to and/or delivered to a treatment site through a handle 218 and shaft 220 of insertion device 212, as discussed above. Guide wire device 262 may include a guide wire 270, which may be coupled to medical device 214, for example, via a slot or opening in a portion of a medical device shaft 228 or medical device handle 226. Additionally, adapter 216 may include an adapter slot or opening 216D. In this aspect, a portion of guide wire 270 may pass through opening 216D. For example, the portion of guide wire 270 may move within opening 216D as medical device shaft 228 moves (e.g., proximally or distally) relative to adapter 216 and port 222 of insertion device 212.

Medical device 214 includes a medical device handle 226 and medical device shaft 228. Medical device handle 226 may include a movable handle portion or a main handle body 226A and a stationary handle portion or a joint (e.g., a ball joint), referred to herein as socket body 226B, with the main handle body 226A being movable relative to and positioned proximal of socket body 226B. As discussed with respect to medical device 14, socket body 226B may abut a portion of adapter 216, and, although not shown, main handle body 226A may be coupled to a plurality of steering wires and an articulation wire. The articulation wire may be coupled to movable body 240 on main handle body 226A. Furthermore, main handle body 226A and socket body 226B may form a ball and socket joint. In this aspect, movement of main handle body 226A relative to socket body 226B controls the movement of one or more steering wires and controls a deflection of distal end 230 of medical device shaft 228, for example, relative to the distal end of insertion device shaft 220. The position of medical device handle 226 relative to port 222 of insertion device handle 218 may also control the position of distal end 230 relative to the distal end of insertion device shaft 220. Furthermore, as discussed above, main handle body 226A may include one or more ports (not shown) or hubs 236B, for example, for coupling of fluid, suction, or energy sources to medical device 214. In this aspect, a user may hold and/or manipulate handle 218 of insertion device 212 with one hand, and may hold and/or manipulate main handle body 226A (e.g., relative to socket body 226B) with another hand.

Moreover, as discussed above with respect to FIGS. 10A-10D, 11A, 11B, and 12A-12C, guide wire device 262 may help to manipulate distal end 230 of medical device shaft 228. For example, guide wire 270 may extend through a portion of medical device shaft 228, for example, to distal end 230. As discussed above, guide wire device 262 includes a handle portion 262A with a casing 262B. A button 262C and a roller 262D may be movable relative to casing 262B of guide wire device 262, for example, may be articulated proximally, distally, or rotated, to control the movement of a pull wire (not shown) in guide wire 270. The movement of the pull wire, and thus the movement of guide wire 270, may help to guide and/or articulate a distal portion of medical device shaft 128, for example, in a plurality of directions.

Various aspects discussed herein may allow for an insertion device and a medical device (e.g., medical device 12) to be delivered to a treatment site, for example, to perform endoscopic submucosal dissection ("ESD") or otherwise treat the treatment site. One or more portions of the medical device (e.g., electrode 38) may be selectively positioned relative to the insertion device by movement of steering wires 50. Moreover, the selective manipulation of one or more wires 50, for example, via movement of main handle body 26A relative to socket body 26B may allow for medical device 14 to approach the treatment site at one or more angles different than insertion device 12, which may help the user to perform the treatment at the treatment site. Specifically, the manipulation of one or more wires 50 may allow for medical device shaft 28 to be deflected (e.g., pivoted or reoriented) up to approximately 90 degrees in each direction relative to distal end 20A of insertion device shaft 20.

In addition to the different angles of approach, medical systems 10, 110, and 210 may provide the user with increased control of the delivered medical device and/or to treat and/or view the treatment site. Wires 50, 150 may be controlled by a medical device handle 26, 126, 226, allowing the user a convenient mechanism to control the position of the medical device shaft relative to the insertion device shaft. Additionally, the force applied and direction of movement (e.g., on main handle body 26A, joystick 164, or main handle body 226A) to the wires may impart different forces and directions of movement to control the amount of pivoting or reorientation of the medical device shaft. The medical systems, including the wires, may allow for the distal portions of the medical device shafts to be pivoted or reoriented to any position or direction within the semispherical range (or greater) extending from the distal end of the insertion device. In some aspects, for example, medical systems 10, 110, and 210 may allow for the distal portion of the medical device shaft to pivot or reorient separate from the insertion device. Furthermore, the medical device handle may be moved longitudinally, e.g., proximally or distally, relative to the insertion device handle to control the longitudinal position of the distal end of the medical device shaft relative to the distal end of the insertion device shaft. An end effector (e.g., electrode 38) positioned at distal end 30 of medical device shaft 28 may also be separately movable or activated, for example, via movable body 40.

As discussed, the medical systems discussed herein may allow for a single operator to control various aspects of the medical systems. For example, referring to FIG. 1, a user may hold and/or control insertion device 12 with a first hand. The user may manipulate control device 24, for example, to deflect distal end 20A of insertion device shaft 20. The user may also hold and/or control medical device 14 with a second hand. The user may manipulate the second hand (e.g., via wrist movement) to control manipulate main handle body 26A relative to socket body 26B, for example, to manipulate distal end 30 of medical device shaft 28. Furthermore, the user may manipulate a finger (e.g., the thumb on the second hand) to manipulate movable body 40, for example, to extend or retract or otherwise actuate an end effector (e.g., electrode 38) relative to distal end 30 of medical device shaft 28 via actuation wire 52. In these aspects, a single user may control various movements and/or functions of medical systems 10, 110, 210. Moreover, the various movements, for example, movement of main handle body 26A relative to socket body 26B, may be intuitive and/or easy for the user to learn and execute during a procedure to treat the treatment site.

Steering wires 50 may be flexible and may be formed of metal (e.g., stainless steel), plastic, or include a shape memory metal (such as nitinol), a shape memory polymer, a polymer, or any combination of biocompatible materials, or another appropriate biocompatible material. Steering wires 50 may be relatively thin compared to medical devices 14, 114, 214. In this aspect, steering wires 50 may not significantly increase the cross-sectional size of medical devices 14, 114, 214, may not otherwise interfere with the movement of medical devices medical devices 14, 114, 214. Similarly, actuation wire 52 may be formed of a metal (e.g., stainless steel), plastic, or include a shape memory metal (such as nitinol), a shape memory polymer, a polymer, or any combination of biocompatible materials, or another appropriate biocompatible material. As discussed above, actuation wire 52 may be conductive, for example, to deliver electrical energy to electrode 38, cautery wire 168, etc. As discussed herein, other components of medical systems 10, 110, 210 may be formed of a plastic, polymer, any combination of biocompatible materials, or another appropriate biocompatible material. In some aspects, various components or portions of components may be formed via an extrusion process, injection molding, additive manufacturing, etc.

Accordingly, various aspects discussed herein may help to improve the efficacy of treatment and/or recovery from a procedure, for example, a procedure to treat a treatment side. Various aspects discussed herein may help to reduce and/or minimize the duration of the procedure, and/or may help reduce risks of inadvertent contact with tissue or other material during delivery, repositioning, or removal of a medical system for the procedure. Additionally, various aspects discussed herein (e.g., medical device 114 and guide wire device 162) may be packaged as a kit to be used to treat a patient, for example, by coupling the kit to an insertion device.

While principles of this disclosure are described herein with reference to illustrative aspects for various applications, it should be understood that the disclosure is not limited thereto. Those having ordinary skill in the art and access to the teachings provided herein will recognize additional modifications, applications, aspects, and substitution of equivalents all fall within the scope of the aspects described herein. Accordingly, the disclosure is not to be considered as limited by the foregoing description.

We claim:

1. A medical device system, comprising
an insertion device, including:
    an insertion device handle, including a port on a handle body, wherein the port includes an extension extending radially outward; and
    an insertion device shaft extending from the insertion device handle, wherein the insertion device shaft includes a working channel connected to the port; and
a medical device, including:
    a medical device handle, including a movable handle portion and a stationary handle portion, wherein the movable handle portion includes a ball portion movably positioned within a cavity in the stationary handle portion;
    an adapter positioned between the port on the insertion device handle of the insertion device and the medical device handle, wherein the adapter includes a projection extending radially inward, wherein the extension is proximal to the projection; and a medical device shaft, wherein the medical device shaft is configured to be delivered through the port in the insertion device handle and through the working channel in the insertion device shaft, wherein movement of the movable handle portion relative to the stationary handle portion controls movement of a distal portion of the medical device shaft.

2. The medical device system of claim 1, further comprising a plurality of steering wires, wherein each of the plurality of steering wires is coupled to the ball portion at a proximal end and to the distal portion of the medical device shaft at a distal end.

3. The medical device system of claim 2, wherein the distal ends of the plurality of steering wires are coupled to a ring at the distal portion of the medical device shaft.

4. The medical device system of claim 3, wherein the plurality of steering wires includes four steering wires coupled to the ball portion, wherein the ball portion includes four wire mounts at locations 90 degrees apart from each other around a circumference of the ball portion, and wherein each wire mount includes a crimping slot to couple each steering wire to the ball portion.

5. The medical device system of claim 1, wherein the medical device includes an actuation wire and a movable body coupled to the actuation wire, wherein the actuation wire is movable relative to the medical device shaft by movement of the movable body relative to the stationary handle portion.

6. The medical device system of claim 5, wherein the medical device includes a distal electrode, and wherein movement of the movable body manipulates the actuation wire to extend or retract the distal electrode relative to a distal end of the medical device shaft.

7. The medical device system of claim 1, wherein the medical device handle includes a fluid port or a cautery hub.

8. The medical device system of claim 1, further comprising a cautery hub on the medical device handle and an actuation wire extending through at least a portion of the medical device handle and the medical device shaft, wherein the actuation wire is electrically connected to the cautery hub.

9. The medical device system of claim 1, wherein the adapter includes an arced portion or is at least partially flexible.

10. The medical device system of claim 9, wherein the adapter is removably coupled to the insertion device and includes one or more slits on a distal portion, and wherein the adapter includes a lock nut that is movable along the distal portion to control a width of each of the one or more slits.

11. The medical device system of claim 1, further comprising a guide wire device, wherein the guide wire device includes a guide wire handle and a guide wire.

12. The medical device system of claim 11, wherein the guide wire includes a main wire portion, a distal wire portion, and a movable pull wire coupled to the distal wire portion, wherein the guide wire handle includes a casing, a roller rotatably coupled to the casing, and a button that is movable within a channel in the roller, and wherein the roller is coupled to the pull wire to control extension or rotation of the pull wire.

13. The medical device system of claim 12, wherein a portion of the pull wire is coupled to the distal wire portion via a coupling, and wherein the coupling extends over less than an entire outer circumference of the portion of the pull wire.

14. The medical device system of claim 1, wherein the movable handle portion is a joystick, and wherein the stationary handle body is a main handle body positioned distal to the joystick.

15. A medical system, comprising:
a medical device, including:
 a medical device handle, including a movable handle portion and a stationary handle portion, wherein the movable handle portion includes a ball portion movably positioned within a cavity in the stationary handle portion;
 a medical device shaft extending from the medical device handle; and
 a plurality of wires, wherein the plurality of wires are coupled to the ball portion of the movable handle portion and to a ring at a distal portion of the medical device shaft, wherein movement of the ball portion of the movable handle portion within the cavity in the stationary handle portion manipulates a distal portion of the medical device shaft; and
a guide wire device, including:
 a guide wire handle; and
 a guide wire,
wherein the medical device shaft includes one or more openings or tubes along one or more outer portions of the medical device shaft configured to receive a portion of the guide wire, wherein the guide wire device includes a main wire portion, a distal wire portion, and a movable pull wire coupled to the distal wire portion,
wherein the guide wire handle includes a casing, a roller rotatably coupled to the casing, and a button that is movable within a channel in the roller, and
wherein the roller is coupled to the pull wire to control extension or rotation of the pull wire.

16. The medical system of claim 15, further comprising:
an insertion device, wherein the insertion device includes:
 an insertion device handle having a port to receive a portion of the medical device shaft and a portion of the guide wire;
 an insertion device shaft extending from the insertion device handle, wherein the insertion device shaft includes a lumen in communication with the port; and
 a control device coupled to a portion of the insertion device handle, wherein the control device is movable to control a position of a distal end of the insertion device shaft.

17. A medical device, comprising:
a medical device handle, including a joystick portion and a stationary handle portion, wherein the joystick portion is positioned distal to the stationary handle portion and includes a ball portion movably positioned within a cavity in the stationary handle portion;
a medical device shaft extending from the medical device handle; and
a plurality of wires, wherein the plurality of wires are coupled to the ball portion of the joystick portion and to a ring at a distal portion of the medical device shaft, wherein movement of the ball portion of the movable handle portion within the cavity in the stationary handle portion manipulates a distal portion of the medical device shaft wherein the ball portion includes:
 a plurality of wire mounts disposed around a circumference of the ball portion, wherein each wire mount includes (i) a crimping slot, (ii) a wire slot, and (iii) a wire opening disposed between the crimping slot and the wire slot.

18. The medical device of claim 17, further comprising:
a movable body coupled to the stationary handle portion; and
an actuation wire extending from the movable body to an end effector at a distal end of the medical device shaft, wherein movement of the movable body controls an extension or retraction of an end effector.

19. The medical device of claim 18, further comprising a guide wire device, wherein the guide wire device includes a guide wire handle and a guide wire.

\* \* \* \* \*